(12) United States Patent
Carpentier et al.

(10) Patent No.: US 8,915,960 B2
(45) Date of Patent: Dec. 23, 2014

(54) PHYSIOLOGIC TRICUSPID ANNULOPLASTY RING

(75) Inventors: Alain F. Carpentier, Paris (FR); William C. Brunnett, Mission Viejo, CA (US); Louis A. Campbell, Santa Ana, CA (US); Da-Yu Chang, Irvine, CA (US); Steven Ford, Laguna Beach, CA (US); John F. Migliazza, Belmont Shore, CA (US); Anand Rao, Tustin, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 170 days.

(21) Appl. No.: 13/221,700

(22) Filed: Aug. 30, 2011

(65) Prior Publication Data

US 2012/0071970 A1    Mar. 22, 2012

Related U.S. Application Data

(60) Provisional application No. 61/378,714, filed on Aug. 31, 2010.

(51) Int. Cl.
*A61F 2/24*    (2006.01)

(52) U.S. Cl.
CPC ....... *A61F 2/2445* (2013.01); *A61F 2230/0052* (2013.01); *A61F 2/2466* (2013.01); *A61F 2230/0039* (2013.01)
USPC ........................................................ 623/2.36

(58) Field of Classification Search
CPC .................................................... A61F 2/2445
USPC ............................................... 623/2.36–2.41
See application file for complete search history.

(56) References Cited

U.S. PATENT DOCUMENTS

| 3,656,185 A | 4/1972 | Carpentier |
| 4,055,861 A | 11/1977 | Carpentier et al. |

(Continued)

FOREIGN PATENT DOCUMENTS

| EP | 0338994 A1 | 10/1989 |
| EP | 0595791 A2 | 5/1994 |

(Continued)

OTHER PUBLICATIONS

Adams David et al. "Large Annuloplasty Rings Facilitate Mitral Valve Repair in Barlow's Disease" Society of Thoracic Surgeons 42nd Annual Meeting Jan. 30-Feb. 1, 2006.

(Continued)

*Primary Examiner* — David Isabella
*Assistant Examiner* — Suba Ganesan
(74) *Attorney, Agent, or Firm* — AnneMarie Kaiser; Pui Tong Ho; Guy Cumberbatch

(57) ABSTRACT

A prosthetic tricuspid remodeling annuloplasty ring for use in tricuspid valve repairs to provide annular support after reconstructive valve surgery. The ring maintains an optimal annular dimension to prevent excessive dilatation of the natural valve annulus while adapting to the dynamic motion of the tricuspid annulus during the cardiac cycle. An exemplary ring features a waveform contour and may be constructed of a titanium core having a varying cross-section for selective flexibility for good Z-axis or out-of plane movement. The "waveform" contour and selective flexibility of the different segments of this ring are designed to adapt to the complex motion of the annulus. This reduces the stress on the anatomical structures and therefore minimizes the risk of arrhythmia and ring dehiscence.

15 Claims, 12 Drawing Sheets

(56) References Cited

U.S. PATENT DOCUMENTS

| | | |
|---|---|---|
| 4,164,046 A | 8/1979 | Cooley |
| 4,217,665 A | 8/1980 | Bex et al. |
| 4,602,911 A | 7/1986 | Ahmadi et al. |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,201,880 A | 4/1993 | Wright et al. |
| 5,258,021 A | 11/1993 | Duran |
| 5,306,296 A | 4/1994 | Wright et al. |
| 5,450,860 A | 9/1995 | O'Connor |
| 5,496,336 A | 3/1996 | Cosgrove et al. |
| 5,593,435 A | 1/1997 | Carpentier et al. |
| 5,607,471 A | 3/1997 | Seguin et al. |
| 5,674,279 A | 10/1997 | Wright et al. |
| 5,776,189 A | 7/1998 | Khalid |
| 5,824,066 A | 10/1998 | Gross |
| 5,824,069 A | 10/1998 | Lemole |
| 5,888,240 A | 3/1999 | Carpentier et al. |
| 5,972,030 A | 10/1999 | Garrison et al. |
| 6,019,739 A | 2/2000 | Rhee et al. |
| 6,024,918 A | 2/2000 | Hendriks et al. |
| 6,102,945 A | 8/2000 | Campbell |
| 6,143,024 A | 11/2000 | Campbell et al. |
| 6,159,240 A | 12/2000 | Sparer et al. |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,602 B1 | 5/2001 | Carpentier et al. |
| 6,250,308 B1 | 6/2001 | Cox |
| 6,258,122 B1 | 7/2001 | Tweden et al. |
| 6,332,893 B1 | 12/2001 | Mortier et al. |
| 6,368,348 B1 | 4/2002 | Gabbay |
| 6,391,054 B2 | 5/2002 | Carpentier et al. |
| 6,406,493 B1 | 6/2002 | Tu et al. |
| 6,419,696 B1 | 7/2002 | Ortiz et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,749,630 B2 | 6/2004 | McCarthy et al. |
| 6,764,510 B2 | 7/2004 | Vidlund et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,908,482 B2 | 6/2005 | McCarthy et al. |
| 6,918,917 B1 | 7/2005 | Nguyen et al. |
| 6,921,407 B2 | 7/2005 | Nguyen et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,101,395 B2 | 9/2006 | Tremulis et al. |
| 7,118,595 B2 | 10/2006 | Ryan et al. |
| 7,125,421 B2 | 10/2006 | Tremulis et al. |
| 7,166,126 B2 | 1/2007 | Spence et al. |
| 7,166,127 B2 | 1/2007 | Spence et al. |
| 7,294,148 B2 | 11/2007 | McCarthy |
| 7,329,280 B2 | 2/2008 | Bolling et al. |
| 7,367,991 B2 | 5/2008 | McCarthy et al. |
| 7,608,103 B2 | 10/2009 | McCarthy |
| 7,879,087 B2 | 2/2011 | Roberts |
| 7,959,673 B2 * | 6/2011 | Carpentier et al. .......... 623/2.36 |
| 7,993,395 B2 | 8/2011 | Vanermen et al. |
| 8,114,155 B2 * | 2/2012 | McCarthy et al. .......... 623/2.36 |
| 8,123,800 B2 | 2/2012 | McCarthy et al. |
| 2002/0129820 A1 | 9/2002 | Ryan et al. |
| 2002/0133180 A1 | 9/2002 | Ryan et al. |
| 2002/0169504 A1 | 11/2002 | Alferness et al. |
| 2002/0173844 A1 | 11/2002 | Alfieri et al. |
| 2003/0033009 A1 | 2/2003 | Gabbay |
| 2003/0040793 A1 | 2/2003 | Marquez |
| 2003/0045929 A1 | 3/2003 | McCarthy et al. |
| 2003/0083742 A1 | 5/2003 | Spence et al. |
| 2003/0093148 A1 | 5/2003 | Bolling et al. |
| 2004/0006384 A1 | 1/2004 | McCarthy |
| 2004/0249452 A1 | 12/2004 | Adams et al. |
| 2004/0249453 A1 | 12/2004 | Cartledge et al. |
| 2005/0004666 A1 | 1/2005 | Alfieri et al. |
| 2005/0043791 A1 | 2/2005 | McCarthy et al. |
| 2005/0131533 A1 | 6/2005 | Alfieri et al. |
| 2005/0182487 A1 | 8/2005 | McCarthy et al. |
| 2005/0192666 A1 | 9/2005 | McCarthy |
| 2005/0256567 A1 | 11/2005 | Lim et al. |
| 2005/0256568 A1 | 11/2005 | Lim et al. |
| 2005/0267572 A1 | 12/2005 | Schoon et al. |
| 2005/0278022 A1 | 12/2005 | Lim |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025858 A1 | 2/2006 | Alameddine |
| 2006/0030885 A1 | 2/2006 | Hyde |
| 2007/0016291 A1 * | 1/2007 | Johnson .......... 623/2.41 |
| 2007/0162111 A1 | 7/2007 | Fukamachi et al. |
| 2008/0086203 A1 | 4/2008 | Roberts |
| 2008/0275551 A1 | 11/2008 | Alfieri |
| 2009/0036979 A1 | 2/2009 | Redmond et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192606 A1 | 7/2009 | Gloss et al. |
| 2009/0287303 A1 | 11/2009 | Carpentier |
| 2010/0179651 A1 | 7/2010 | Fawzy et al. |
| 2011/0022169 A1 | 1/2011 | Ryan et al. |
| 2011/0160849 A1 | 6/2011 | Carpentier et al. |

FOREIGN PATENT DOCUMENTS

| | | |
|---|---|---|
| EP | 0860151 A1 | 8/1998 |
| EP | 1034753 A1 | 9/2000 |
| FR | 2708458 A1 | 2/1995 |
| WO | 9503757 | 2/1995 |
| WO | 98/14138 A1 | 4/1998 |
| WO | 99/49816 A1 | 10/1999 |
| WO | 01/08608 A1 | 2/2001 |
| WO | 0119292 A1 | 3/2001 |
| WO | 0126586 A1 | 4/2001 |
| WO | 0147438 A1 | 7/2001 |
| WO | 0187191 A1 | 11/2001 |
| WO | 0203892 A1 | 1/2002 |
| WO | 03020178 A1 | 3/2003 |
| WO | 03041617 A1 | 5/2003 |
| WO | 2004/004607 A1 | 1/2004 |
| WO | 2005/034813 A2 | 4/2005 |
| WO | 2005/110290 A1 | 11/2005 |
| WO | 2007-050506 A1 | 5/2007 |

OTHER PUBLICATIONS

Alonso-Lei M.D. et al. "Adjustable Annuloplasty for Tricuspid Insufficiency" The annals of Thoracic Surgery vol. 46 No. 3 pp. 368-369 Sep. 1988.

Bolling et al. Surgical Alternatives for Heart Failure The Journal of Heart and Lung Transplantation vol. 20 No. 7 pp. 729-733 2001.

Bolling Mitral Valve Reconstruction in the Patient With Heart Failure Heart Failure Reviews 6 pp. 177-185 2001.

Carpentier et al. "The 'Physio-Ring': An Advanced Concept in Mitral Valve Annuloplasty" Society of Thoracic Surgeons 31st Annual meeting Jan. 30-Feb. 2, 1995.

Carpentier et al. Reconstructive Valve Surgery Chapter 19—Reconstructive Techniques ISBN No. 978-0-7216-9168-8 Sanders Elsevier Publishing Maryland Heights Missouri 2010.

Carpentier-Edwards Classic Annuloplasty Ring With Duraflo Treatment Models 4425 and 4525 for Mitral and Tricuspid Valvuloplsty Baxter Healthcare Corporation 1998.

Carpentier-Edwards Pyshio Annuloplasty Ring Edwards Lifesciences Corporation 2003.

(56) References Cited

OTHER PUBLICATIONS

Cochran et al. Effect of Papillary Muscle Position on Mitral Valve Function: Relationship to Homografts The Society of Thoracic Surgeons pp. 5155-5161 1998.
D.C. Miller, M.D. "Ischemic Mitral Regurgitation Redux—To Repair or Replace?" The Journal of Thoracic & Cardiovascular Surgery Dec. 2001 vol. 122 No. 6 pp. 1059-1062.
Edwards Lifesciences Carpentier-Edwards Classic Mitral Annuloplasty Ring www.ctsnet.orgEdwardsproduct702.
Flachskampf Frank A. et al. "Analysis of Shape and Motion of the Mitral Annulin Subjects With and Without Cardiomyopathy by Echocardiographic 3-Dimensional Reconstruction" American Society of Echocardiography 0894-73172000.
Gatti et al. Preliminary Experience in Mitral Valve Repair Using the Cosgrove-Edwards Annuloplasty Ring Interactive Cardiovascular and Thoracic Surgery vol. 2(3) pp. 256-261 2003.
Melo et al.; "Atrioventricular Valve Repair Using Externally Adjustable Flexible Rings" The Journal of Thoracic and Cardiovascular Surgery vol. 11 No. 5 1333-1337 Nov. 1995.
MGH Study Shows Mitral Valve Prolapse Not a Stroke Risk Factor Massachusetts General Hospital pp. 1-3 Jun. 1999.
Qin JX, Jones M, Shiota T, Greenberg NL, Tsujino H, Firstenberg MS, Gupta PC, Zetts AD, Xu Y, Ping Sun J, Cardon LA, Odabashian JA, Flamm SD, White RD, Panza JA, Thomas JD. Validation of real-time three-dimensional echocardiography for quantifying left ventricular volumes in the presence of a left ventricular aneurysm: in vitro and in vivo studies. J Am Coll Cardiol 2000;36:900-907.
Salgo et al. Effect of Annular Shape on Leaflet Curvature in Reducing Mitral Leaflet American Heart Association Circulation 2002; pp. 106-711.
Seguin et al. Advance in Mitral Valve Repair Using a Device Flexible in Three Dimensions The St. Jude Medical—Seguin Annuloplasty Ring ASAIO Journal vol. 42 No. 6 pp. 368-371 1996.
Smolens et al. Mitral Valve Repair in Heart Failure The European Journal of Heart Failure 2 pp. 365-371 2000.
Techniques for 3D Quantitative Echocardiography University of Washington Cardiovascular Research & Training Center Cardiac Imaging Research Lab pp. 1-5 Oct. 2003.
Watanabe Nozomi et al. "Mitral AnnulFlattens in Ischemic Mitral Regurgitation: Geometric Differences Between Inferior and Anterior Myocardial Infarction: A Real-Time 3-Dimensional Echocardiographic Study" American Heart Association © 2005; ISSN: 1524-4539.
International Search Report from corresponding international application No. PCT/US2010/061729 mailed Oct. 24, 2011.

* cited by examiner

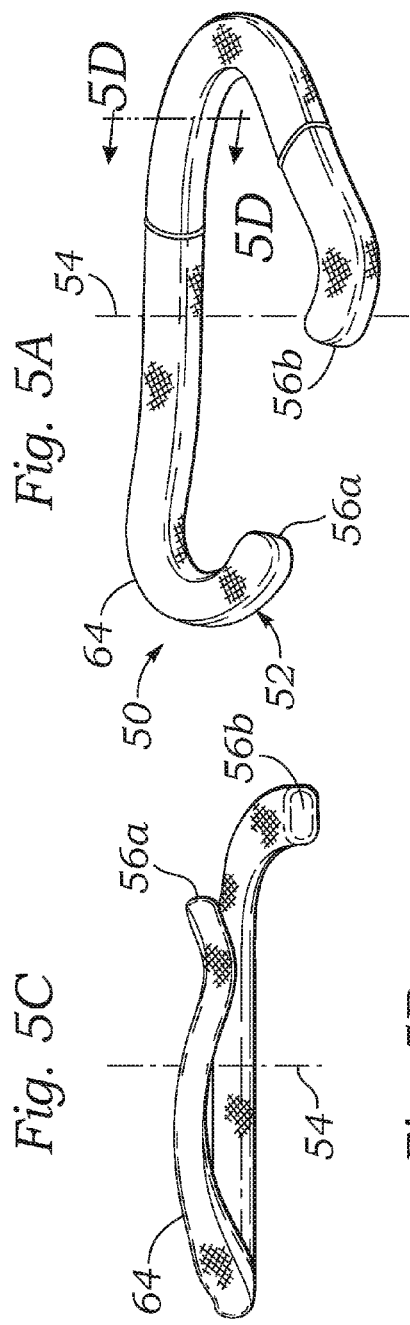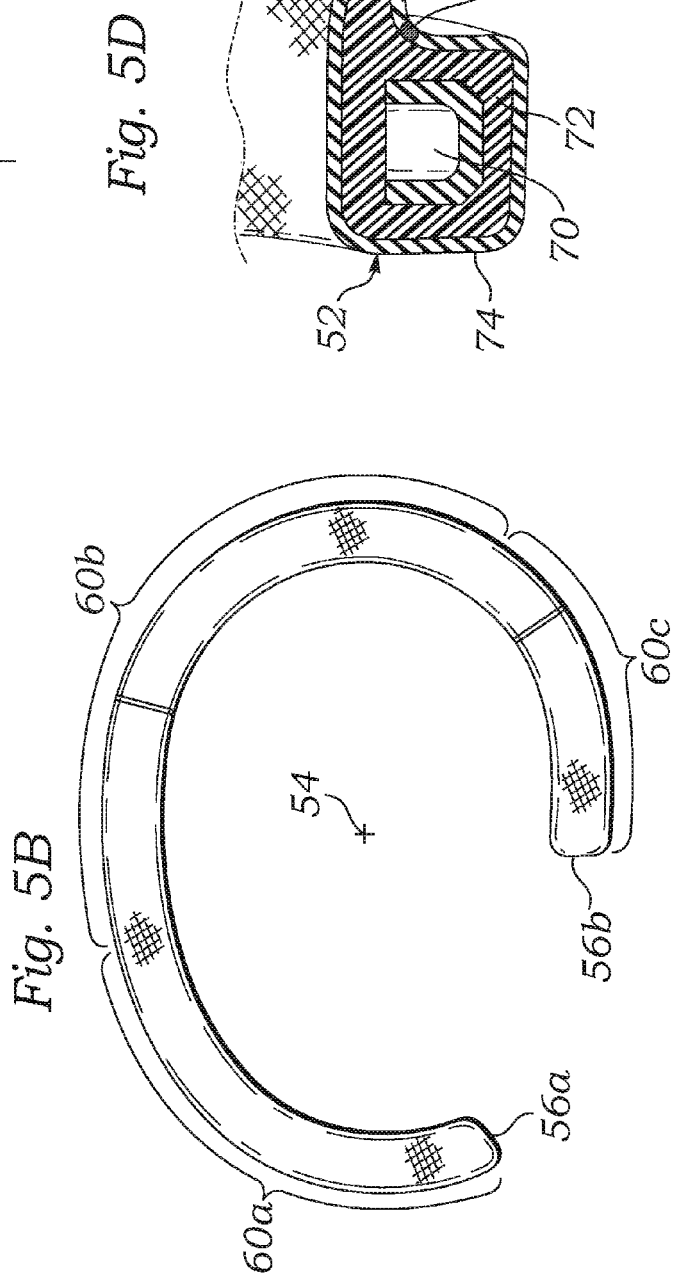

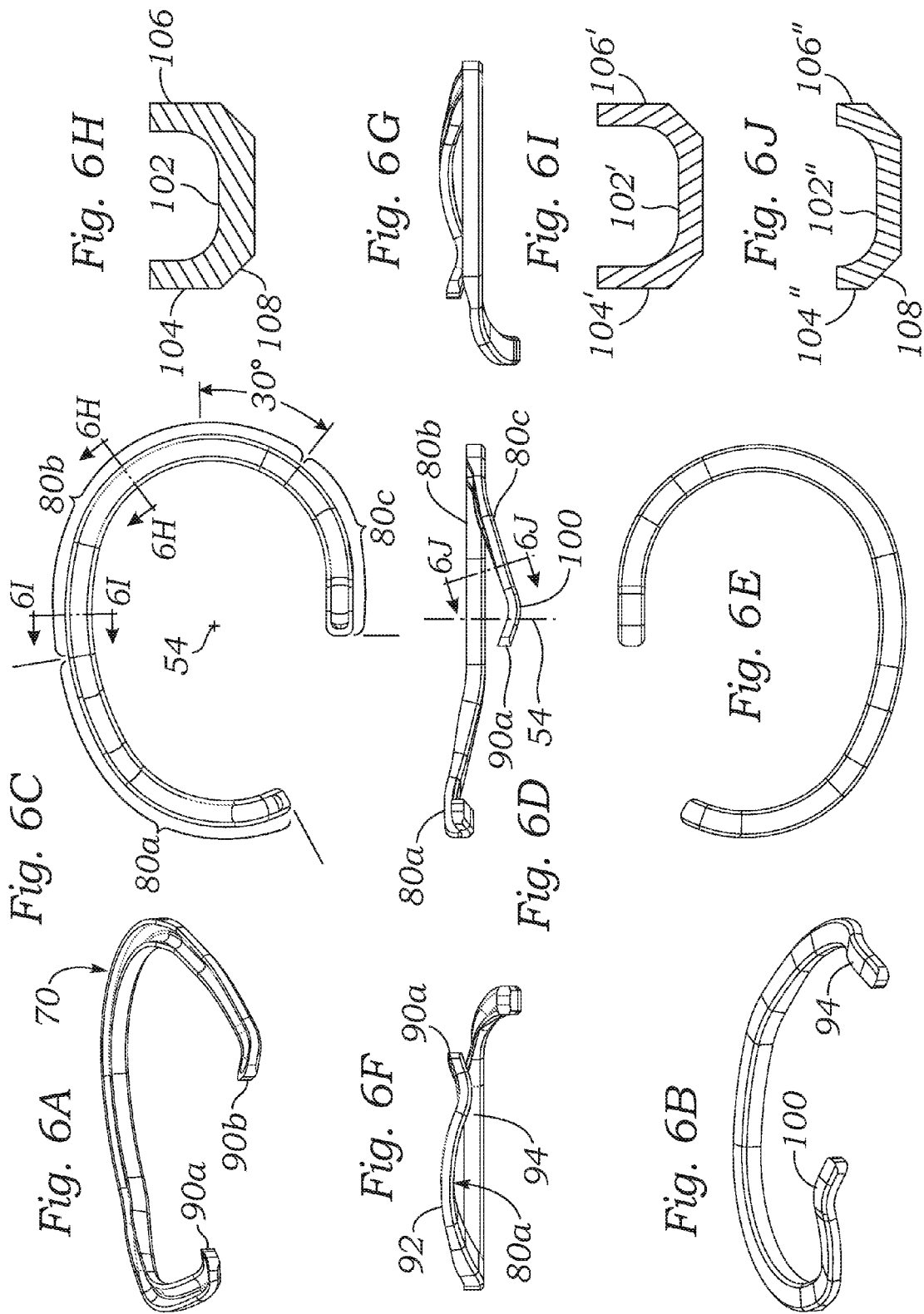

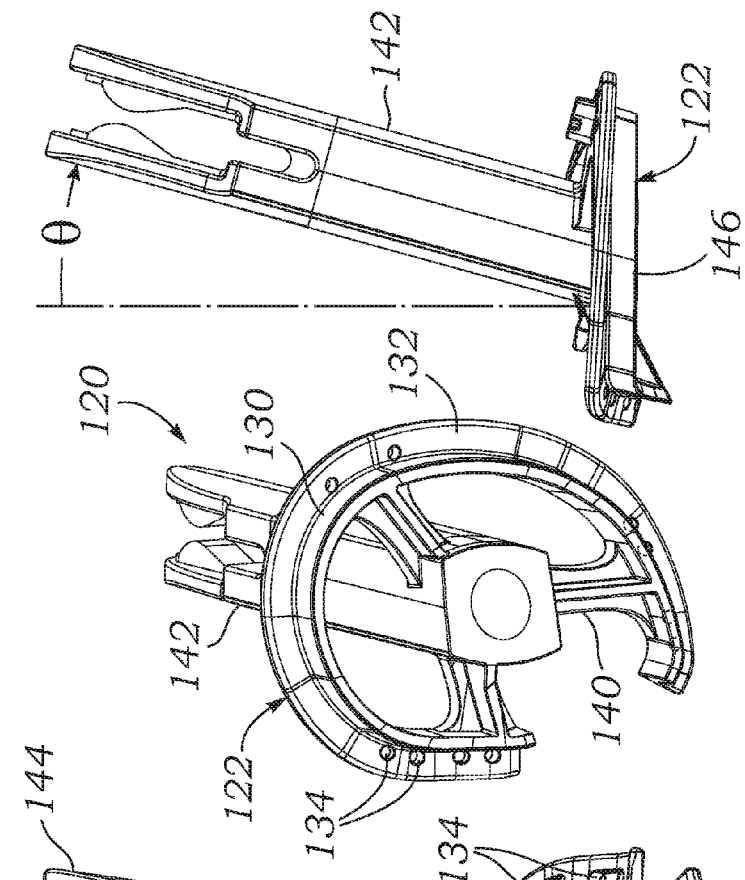

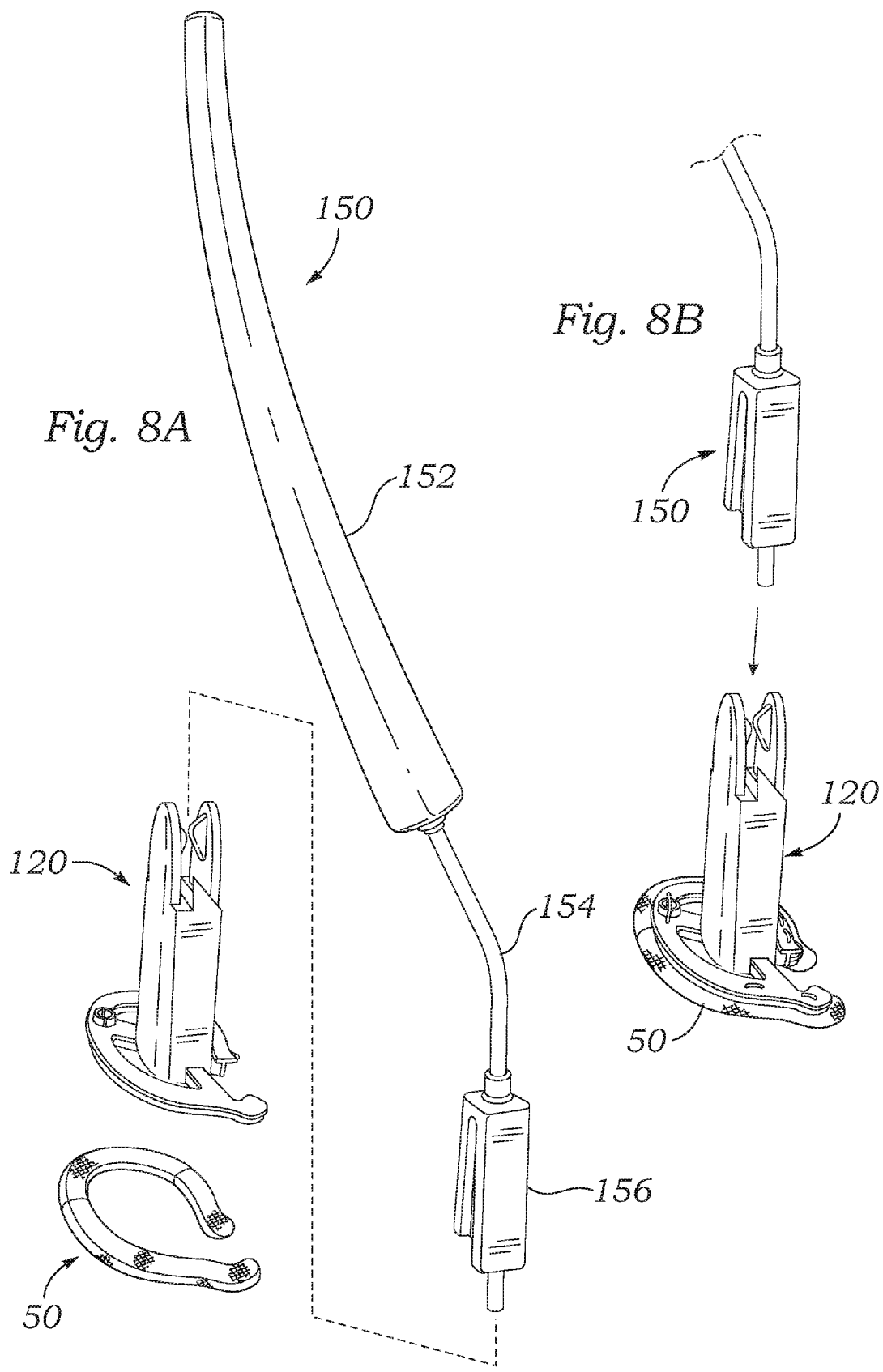

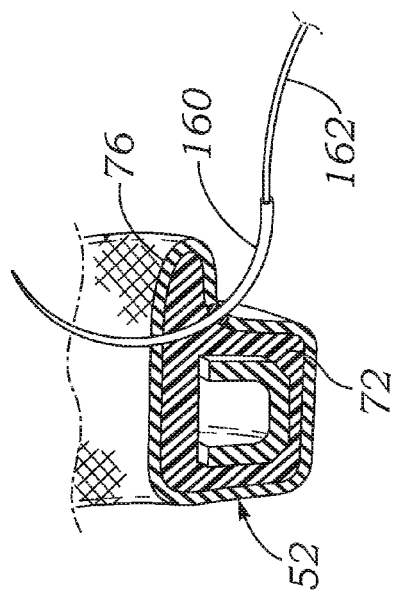
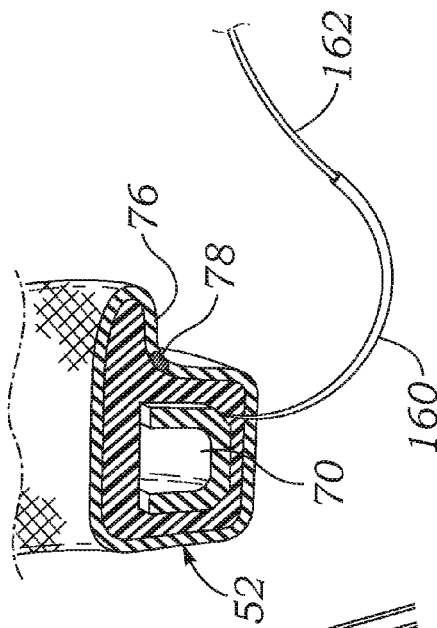
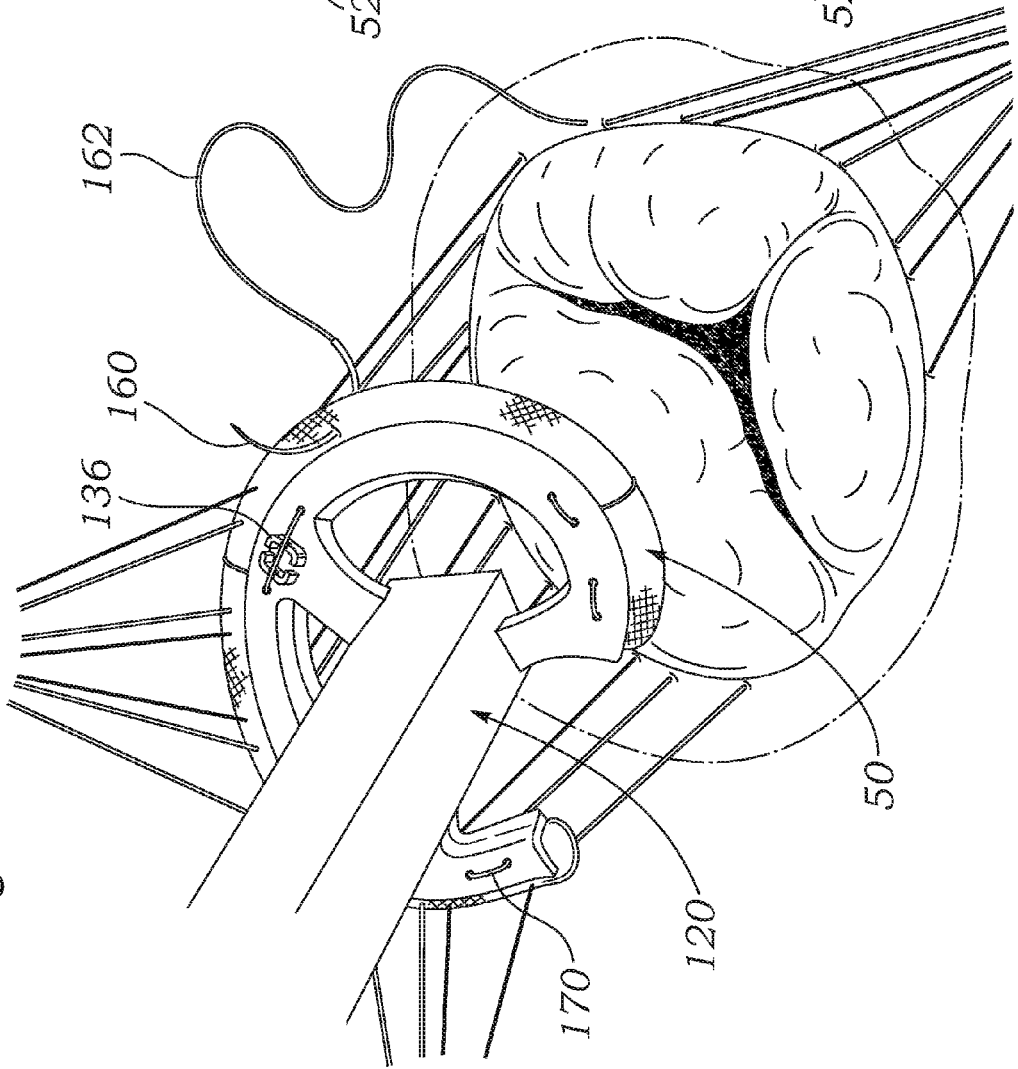

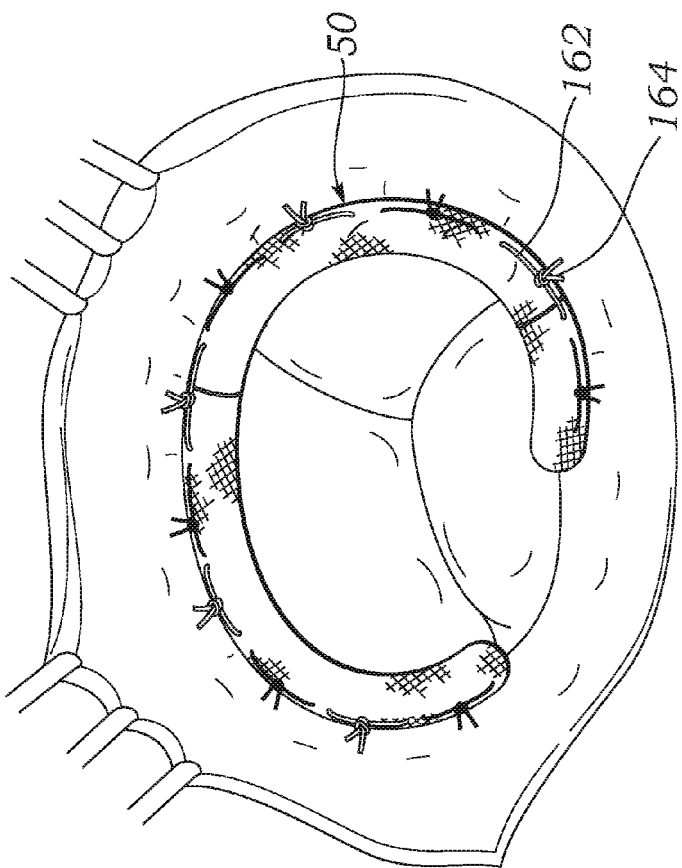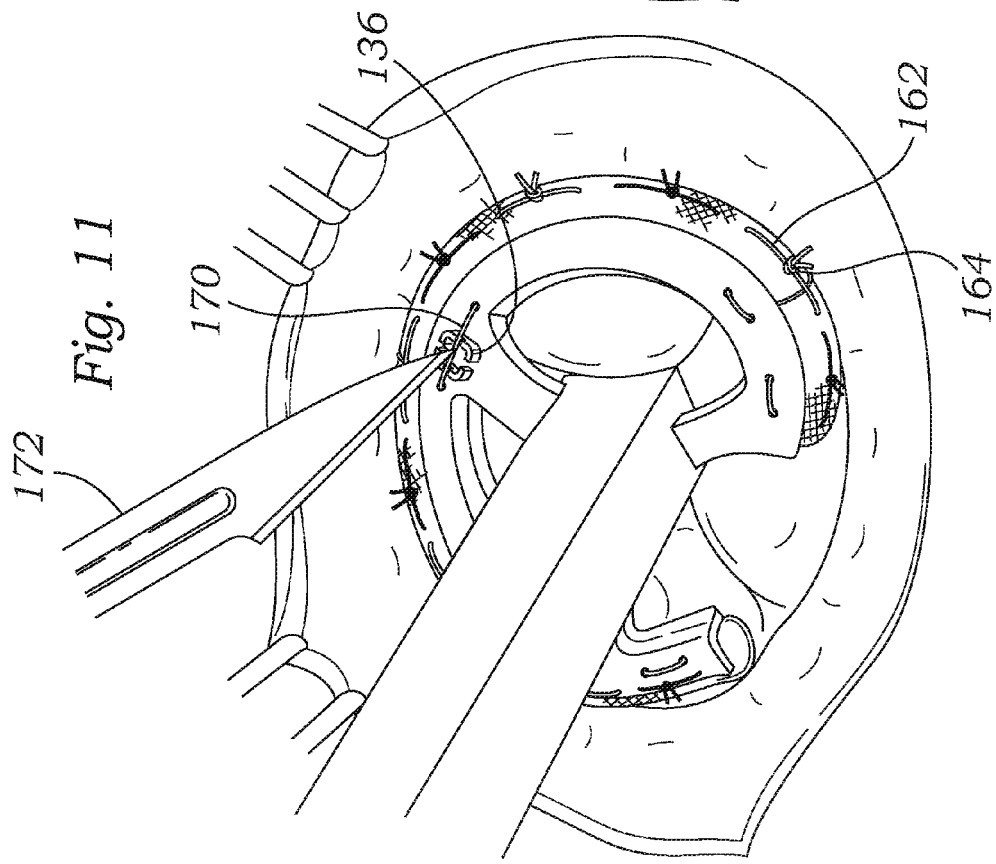

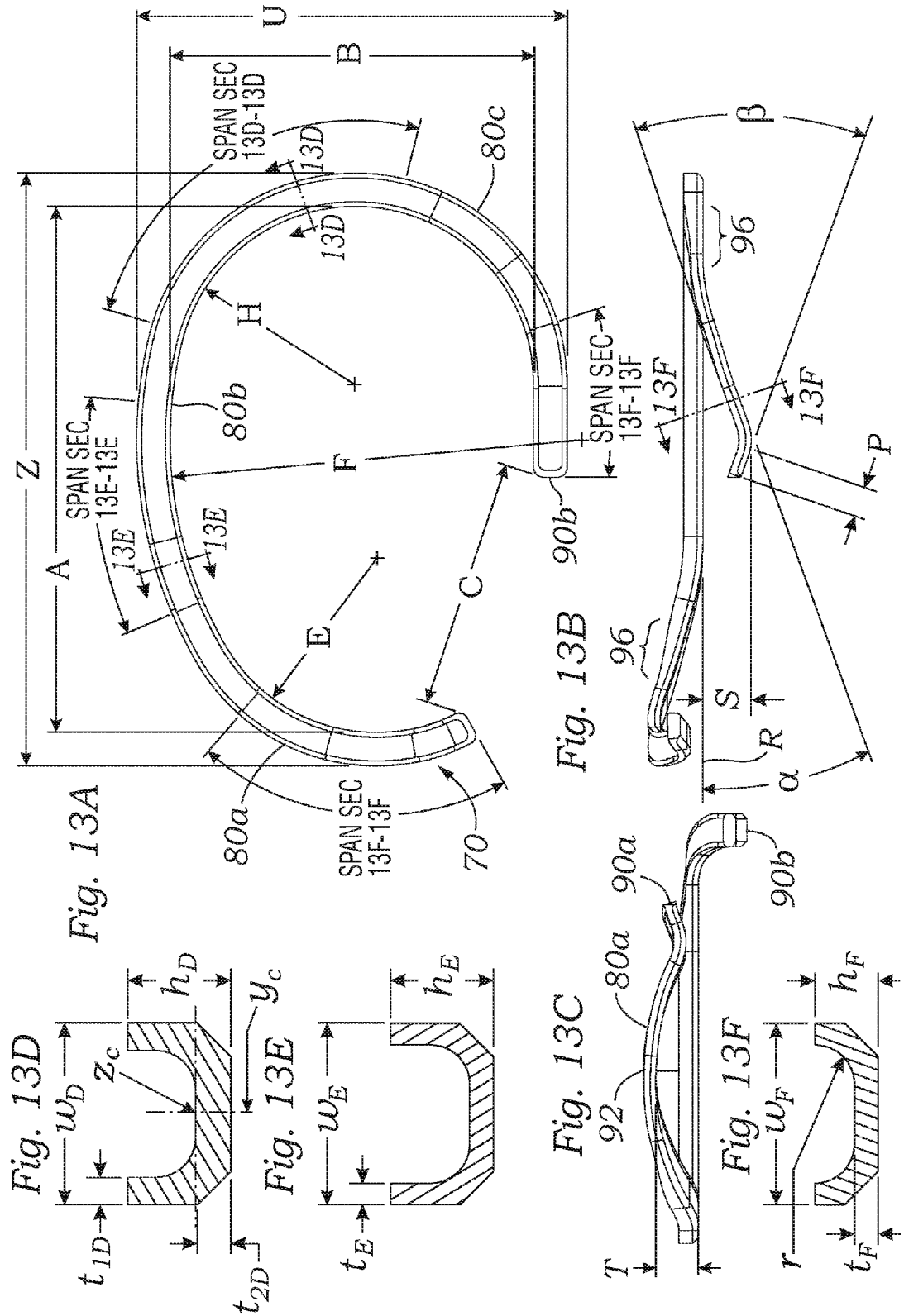

PHYSIOLOGIC TRICUSPID ANNULOPLASTY RING

RELATED APPLICATIONS

The present application claims priority under 35 U.S.C. §119 to U.S. Provisional Application No. 61/378,714, filed on Aug. 31, 2010.

FIELD OF THE INVENTION

The present invention relates generally to implantable medical devices and particularly to a tricuspid annuloplasty ring.

BACKGROUND OF THE INVENTION

In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

Heart valve disease is a widespread condition in which one or more of the valves of the heart fails to function properly. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques may be used to repair a diseased or damaged valve. In a valve replacement operation, the damaged leaflets are excised and the annulus sculpted to receive a replacement valve. Another less drastic method for treating defective valves is through repair or reconstruction, which is typically used on minimally calcified valves. One repair technique that has been shown to be effective in treating incompetence is ring annuloplasty, first introduced by Carpentier in 1968, in which the deformed valve annulus is reshaped by attaching a prosthetic annuloplasty repair segment or ring to the valve annulus. The annuloplasty ring is designed to support the functional changes that occur during the cardiac cycle: maintaining coaptation and valve integrity to prevent reverse flow while permitting good hemodynamics during forward flow.

The annuloplasty ring typically comprises an inner substrate of a metal such as rods or bands of stainless steel or titanium, or a flexible material such as silicone rubber or Dacron cordage, covered with a biocompatible fabric or cloth to allow the ring to be sutured to the fibrous annulus tissue. Annuloplasty rings may be stiff or flexible, split or continuous, and may have a variety of shapes, including circular, D-shaped, C-shaped, or kidney-shaped. Examples are seen in U.S. Pat. Nos. 5,041,130, 5,104,407, 5,201,880, 5,258,021, 5,607,471 and, 6,187,040 B1. Most annuloplasty rings are formed in a plane, with some D-shaped mitral rings being bowed along their straight side to conform to the shape of the annulus at that location. Whether totally flexible, rigid, or semi-rigid, annuloplasty rings have been associated with a 10% to 15% ring dehiscence incidence at 10 years, thus requiring a reoperation. The present invention is intended to reduce this complication.

For the purposes of anatomic orientation, please refer to FIG. 1, which is a schematic representation of the atrioventricular (AV) junctions within the heart and the body in the left anterior oblique projection. The body is viewed in the upright position and has 3 orthogonal axes: superior-inferior, posterior-anterior, and right-left (lateral).

FIG. 2 is a cutaway view of the heart from the front, or anterior, perspective, with most of the primary structures marked. As is well known, the pathway of blood in the heart is from the right atrium to the right ventricle through the tricuspid valve, to and from the lungs, and from the left atrium to the left ventricle through the mitral valve. The present application has particular relevance to the repair of the tricuspid valve, which regulates blood flow between the right atrium and right ventricle, although certain aspects may apply to repair of other of the heart valves. The tricuspid and mitral valves together define the AV junctions.

As seen in FIG. 2, four structures embedded in the wall of the heart conduct impulses through the cardiac muscle to cause first the atria then the ventricles to contract. These structures are the sinoatrial node (SA node), the atrioventricular node (AV node), the bundle of His, and the Purkinje fibers. On the rear wall of the right atrium is a barely visible knot of tissue known as the sinoatrial, or SA node. This tiny area is the control of the heart's pacemaker mechanism. Impulse conduction normally starts in the SA node which generates a brief electrical impulse of low intensity approximately 72 times every minute in a resting adult. From this point the impulse spreads out over the sheets of tissue that make up the two atria, exciting the muscle fibers as it does so. This causes contraction of the two atria and thereby thrusts the blood into the empty ventricles. The impulse quickly reaches another small specialized knot of tissue known as the atrioventricular, or AV node, located between the atria and the ventricles. This node delays the impulse for about 0.07 seconds, which is exactly enough time to allow the atria to complete their contractions. When the impulses reach the AV node, they are relayed by way of the several bundles of His and Purkinje fibers to the ventricles, causing them to contract. As those of skill in the art are aware, the integrity and proper functioning of the conductive system of the heart is critical for good health.

FIG. 3 is a schematic view of the tricuspid valve orifice seen from its inflow side (from the right atrium), with the peripheral landmarks labeled as: antero septal commissure, anterior leaflet, antero posterior commissure, posterior leaflet, postero septal commissure, and septal leaflet. Contrary to traditional orientation nomenclature, the tricuspid valve is nearly vertical, as reflected by these sector markings.

From the same viewpoint, the tricuspid valve 20 is shown surgically exposed in FIG. 4 with an annulus 22 and three leaflets 24a, 24b, 24c extending inward into the flow orifice. Chordae tendineae 26 connect the leaflets to papillary muscles located in the right ventricle to control the movement of the leaflets. The tricuspid annulus 22 is an ovoid-shaped fibrous ring at the base of the valve that is less prominent than the mitral annulus, but larger in circumference.

Reflecting their true anatomic location, the three leaflets in FIG. 4 are identified as septal 24a, anterior 24b, and posterior (or "mural") 24c. The leaflets join together over three prominent zones of apposition, and the peripheral intersections of these zones are usually described as commissures 28. The leaflets 24 are tethered at the commissures 28 by the fan-shaped chordae tendineae 26 arising from prominent papillary muscles originating in the right ventricle. The septal leaflet 24a is the site of attachment to the fibrous trigone, the fibrous "skeletal" structure within the heart. The anterior leaflet 24b, largest of the 3 leaflets, often has notches. The posterior leaflet 24c, smallest of the 3 leaflets, usually is scalloped.

The ostium 30 of the right coronary sinus opens into the right atrium, and the tendon of Todaro 32 extends adjacent thereto. The AV node 34 and the beginning of the bundle of His 36 are located in the supero-septal region of the tricuspid valve circumference. The AV node 34 is situated directly on the right atrial side of the central fibrous body in the muscular portion of the AV septum, just superior and anterior to the ostium 30 of the coronary sinus 30. Measuring approximately 1.0 mm×3.0 mm×6.0 mm, the node is flat and generally oval shaped. The AV node 34 is located at the apex of the triangle of Koch 38, which is formed by the tricuspid annulus 22, the ostium 30 of the coronary sinus, and the tendon of Todaro 32. The AV node 34 continues on to the bundle of His 36, typically via a course inferior to the commissure 28 between the septal 24a and anterior 24b leaflets of the tricuspid valve; however, the precise course of the bundle of His 36 in the vicinity of the tricuspid valve may vary. Moreover, the location of the bundle of His 36 may not be readily apparent from a resected view of the right atrium because it lies beneath the annulus tissue.

The triangle of Koch 38 and tendon of Todaro 32 provide anatomic landmarks during tricuspid valve repair procedures. A major factor to consider during surgery is the proximity of the conduction system (AV node 34 and bundle of His 36) to the septal leaflet 24a. Of course, surgeons must avoid placing sutures too close to or within the AV node 34. C-shaped rings are good choices for tricuspid valve repairs because they allow surgeons to position the break in the ring adjacent the AV node 34, thus avoiding the need for suturing at that location.

One prior art rigid C-shaped ring of the prior art is the Carpentier-Edwards Classic® Tricuspid Annuloplasty Ring sold by Edwards Lifesciences Corporation of Irvine, Calif. Although not shown, the Classic® ring has an inner titanium core (not shown) covered by a layer of silicone and fabric. Rings for sizes 26 mm through 36 mm in 2 mm increments have outside diameters (OD) between 31.2-41.2 mm, and inside diameters (ID) between 24.3-34.3 mm. These diameters are taken along the "diametric" line spanning the greatest length across the ring because that is the conventional sizing parameter. A gap between free ends in each Classic® ring provides the discontinuity to avoid attachment over the AV node 34. The gap for the various sizes ranges between about 5-8 mm, or between about 19%-22% of the labeled size, and preferably larger than the AV node 34. The Classic® ring is shaped and designed for downsizing diseased annuluses with Rheumatic Fever damage. The surgeon typically attaches the Classic® ring to the tricuspid annulus using single loop interrupted sutures along the outer edge of the ring. Despite the gap between the ends of the ring, some surgeons are uncomfortable passing sutures so close to the conductive AV node 34, particularly considering the additional concern of the bundle of His 36. Indeed, a small percentage of Classic® ring implants trigger conduction disturbances and arrhythmias.

Despite numerous designs presently available or proposed in the past, there is a need for a prosthetic tricuspid ring that better harmonizes with the physiologic features of the tricuspid annulus, and in particular for a prosthetic tricuspid ring that better fits the contours of the tricuspid annulus and presents selective flexibility to reduce the stress in the attachment sutures, while at the same time reduces the risk of inadvertently passing a suture through the critical physiologic structures within the heart that conduct impulses. There is also a need for a remodeling tricuspid ring for treating a dilated annulus with functional tricuspid regurgitation.

SUMMARY OF THE INVENTION

The present invention provides a physiologic tricuspid annuloplasty ring including a ring body generally arranged in a plane and about an axis along an inflow-outflow direction, the ring body being discontinuous so as to define a first free end and a second free end separated across a gap.

The improved physiologic tricuspid annuloplasty ring provides a waveform configuration to reduce constraints in certain areas that have led to dehiscence or suture pull-out in previous rings. At the same time, a more flexible "shock absorbing" structure permits deformation of the ring in different areas depending on the individual constraints and annulus movements of individual patients. Also, a more flexible septal end reduces the incidence of conduction tissue disorders and arrhythmias that have been seen with more rigid rings. Finally, these advantageous aspects combine with structural features that preserve the overall remodeling result intended.

The physiologic tricuspid annuloplasty ring disclosed herein is for use in tricuspid valve repairs to provide remodeling after annuloplasty surgery. The ring maintains a fixed maximum annular dimension to prevent excessive dilatation of the natural valve annulus while adapting to the dynamic motion of the tricuspid annulus during the cardiac cycle. In general, the rings disclosed herein are designed to maximize in-plane annular stiffness while allowing the natural out of plane motion taken by the annulus to take place with little resistance. An exemplary ring features a waveform contour and may be constructed of a titanium core having a varying cross-section for selective flexibility. The ring's sewing cuff consists of silicone rubber covered with a woven polyester cloth. Transverse colored thread markings on the ring preferably indicate the antero posterior and the postero septal commissures, and a dashed line of colored threads indicates the edge of the sewing cuff and the outflow side of the ring. The "waveform" contour and selective flexibility of the different segments of this ring are designed to adapt to the complex motion of the annulus. This reduces the stress on the anatomical structures and therefore minimizes the risk of arrhythmia and ring dehiscence. The ring is open at the antero septal commissure to avoid the conduction system.

In accordance with one aspect disclosed herein, a prosthetic tricuspid annuloplasty ring comprises an asymmetric generally ovoid ring body surrounding an axis along an inflow-outflow direction, with a first free end located adjacent an antero-septal commissure when implanted and a second free end located at a septal point. The ring body extends in a clockwise direction as seen looking at an inflow side from the first free end around a first segment, a second segment, and a third segment that terminates in the second free end. The ring body includes an inner core member which, in the second segment, has a U-shaped radial cross-section open in the inflow direction with a first height $h_1$, and which, in the first and third segments, also has a U-shaped cross-section open in the inflow direction with lesser heights relative to $h_1$. The ring body can include a suture-permeable interface surrounding the core member, and an outer fabric covering. The suture-permeable interface includes an outwardly projecting flange on an inflow edge of the ring body, and the ring further includes a visible marker line on the fabric cover at the base of the flange on its outflow side. The core member can have gradual transitions between the U-shaped radial cross-section of the first height $h_1$ and the U-shaped cross-sections of lesser heights. At any one point around the core member the U-shaped radial cross-sections include side walls having a thickness $t_1$ and a web having a thickness $t_2$, and the thicknesses $t_1$ and $t_2$ vary gradually around the core member. For instance, the thicknesses $t_1$ and $t_2$ taper down from the second segment to both the first and third segments. The ring body can include an inner core member having an in-plane bending stiffness measured by moving one free end in the radial plane with respect to the other free end that is at least 10 times the torsional out-of-plane bending stiffness measured by moving one free end vertically with respect to the other free end. Further, the second segment of the ring body is generally planar with the first segment rising up therefrom in a complex curve and the third segment descending down therefrom in a complex curve.

Another prosthetic tricuspid annuloplasty ring disclosed in the present application also includes an asymmetric generally ovoid ring body surrounding an axis along an inflow-outflow direction with a first free end located adjacent an antero-septal commissure when implanted and a second free end located at a septal point. The ring body extends in a clockwise direction as seen looking at an inflow side from the first free end around a first segment, a second segment, and a third segment that terminates in the second free end, wherein the second segment is generally planar with the first segment rising up therefrom in a complex curve and the third segment descending down therefrom in a complex curve. The complex curves in both the first and third segments can terminate in upturned free ends. The ring body can include a suture-permeable interface surrounding the core member, and an outer fabric covering. The suture-permeable interface includes an outwardly projecting flange on an inflow edge of the ring body, and the ring further includes a visible marker line on the fabric cover at the base of the flange on its outflow side. The ring body can include an inner core member which, in the second segment, has a U-shaped radial cross-section open in the inflow direction with a first height $h_1$, and which, in the first and third segments, also has a U-shaped cross-section open in the inflow direction with lesser heights relative to $h_1$. The core member can have gradual transitions between the U-shaped radial cross-section of the first height $h_1$ and the U-shaped cross-sections of lesser heights. At any one point around the core member the U-shaped radial cross-sections include side walls having a thickness $t_1$ and a web having a thickness $t_2$, and the thicknesses $t_1$ and $t_2$ vary gradually around the core member. The ring body can include an inner core member having an in-plane bending stiffness measured by moving one free end in the radial plane with respect to the other free end that is at least 10 times the torsional out-of-plane bending stiffness measured by moving one free end vertically with respect to the other free end.

Another alternative prosthetic tricuspid annuloplasty ring disclosed herein includes a ring body surrounding a vertical axis along an inflow-outflow direction and a radial plane perpendicular thereto, with a first free end and a second free end separated across a gap. The ring body extends at least half-way around the vertical axis. The ring body includes an inner core member having an in-plane bending stiffness measured by moving one free end in the radial plane with respect to the other free end that is at least 10 times the torsional out-of-plane bending stiffness measured by moving one free end vertically with respect to the other free end. Preferably, the core member has an in-plane bending stiffness that is between about 10-200 times the torsional out-of-plane bending stiffness, or between about 20-60 times the torsional out-of-plane bending stiffness, or between about 20-40 times the torsional out-of-plane bending stiffness. The second segment of the ring body is generally planar with the first segment rising up therefrom in a complex curve and the third segment descending down therefrom in a complex curve. The complex curves in both the first and third segments can terminate in upturned free ends. The ring body can include a suture-permeable interface surrounding the core member and an outer fabric covering. The suture-permeable interface includes an outwardly projecting flange on an inflow edge of the ring body, and the ring further includes a visible marker line on the fabric cover at the base of the flange on its outflow side. The ring body can include an inner core member which, in the second segment, has a U-shaped radial cross-section open in the inflow direction with a first height $h_1$, and in the first and third segments, also has a U-shaped cross-section open in the inflow direction with lesser heights relative to $h_1$. The core member can have gradual transitions between the U-shaped radial cross-section of the first height $h_1$ and the U-shaped cross-sections of lesser heights. At any one point around the core member the U-shaped radial cross-sections can include side walls having a thickness $t_1$ and a web having a thickness $t_2$, and the thicknesses $t_1$ and $t_2$ vary gradually around the core member.

A still further alternative prosthetic tricuspid annuloplasty ring comprises an asymmetric generally ovoid ring body surrounding an axis along an inflow-outflow direction with a first free end located adjacent an antero-septal commissure when implanted and a second free end located at a septal point. In this ring, the ring body extends in a clockwise direction as seen looking at an inflow side from the first free end around a first segment, a second segment, and a third segment that terminates in the second free end, and the ring body includes an inner core member in the second segment of which has a U-shaped radial cross-section open in the inflow direction with a first height $h_1$ and in the first and third segments of which also has U-shaped cross-sections open in the inflow direction with lesser heights relative to $h_1$. The core member may have gradual transitions between the U-shaped radial cross-section of the first height $h_1$ and the U-shaped cross-sections of lesser heights. Desirably, at any one point around the core member the core U-shaped radial cross-sections include side walls having a thickness $t_1$ and a web having a thickness $t_2$, and the thicknesses $t_1$ and $t_2$ vary gradually around the core member. For instance, the thicknesses $t_1$ and $t_2$ taper down from the second segment to both the first and third segments.

Another prosthetic tricuspid annuloplasty ring of the present application features an asymmetric generally ovoid ring body surrounding an axis along an inflow-outflow direction with a first free end located adjacent an antero-septal commissure when implanted and a second free end located at a septal point. The ring body includes an inner core member having sufficient stiffness to remodel the tricuspid annulus, a suture-permeable interface surrounding the core member, and an outer fabric covering. The suture-permeable interface includes an outwardly projecting flange on an inflow edge of the ring body, and the ring further includes a visible marker line on the fabric cover at the base of the flange on its outflow side.

Finally, a combination of a prosthetic tricuspid annuloplasty ring and a holder therefore is also disclosed herein. The annuloplasty ring has an asymmetric generally ovoid ring body surrounding an axis along an inflow-outflow direction with a first free end located adjacent an antero-septal commissure when implanted and a second free end located at a septal point. The ring body extends in a clockwise direction as seen looking at an inflow side from the first free end around a first segment, a second segment, and a third segment that terminates in the second free end, and wherein the second segment is generally planar with the third segment descending down therefrom and terminating the second free end which is upturned. The holder includes a relatively rigid template including a mounting ring that defines a channel for receiving the ring body and is identically shaped and has two free ends. A plurality of spokes extend inward from the mounting ring, and a central hub to which the spokes connect has a connector for a delivery handle. The holder may further include a single cutting guide disposed on an upper surface of the mounting ring at a location approximately diametrically opposed from a gap between the two free ends of the mounting ring.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIGS. 5A-5D are perspective, top plan, anterior elevational, and sectional views, respectively, of an exemplary physiologic tricuspid annuloplasty ring of the present application;

FIGS. 6A-6J are various views of an exemplary inner core member of the tricuspid annuloplasty ring of FIG. 5;

FIGS. 7A-7C are different perspective views of a ring holder for delivering the tricuspid annuloplasty ring of FIG. 5 to a tricuspid annulus for implant, and FIG. 7D is an orthogonal view of the ring holder;

FIG. 8A is an exploded perspective view of the tricuspid annuloplasty ring, holder, and a delivery handle that attaches to the holder, and FIG. 8B shows the ring and holder assembled with the handle disconnected therefrom;

FIG. 9 shows a step in a procedure for implanting the tricuspid annuloplasty ring at a tricuspid annulus, and in particular shows the technique of pre-installing implant sutures at the annulus and threading them through corresponding locations around the ring;

FIG. 10A is a radial cross-section through a tricuspid annuloplasty ring of the present application showing proper threading of a suture needle through an outer sewing flange, while FIG. 10B shows an improper technique;

FIG. 11 shows the tricuspid annuloplasty ring after implant sutures are tied off and before release of the ring holder;

FIG. 12 shows the tricuspid annuloplasty ring fully implanted at the tricuspid annulus;

FIGS. 13A-13F are top plan, septal, anterior elevational and sectional views, respectively, of the inner core member of an exemplary tricuspid annuloplasty ring disclosed herein with a number of dimensions indicated;

DETAILED DESCRIPTION OF THE PREFERRED EMBODIMENTS

Figure 4:
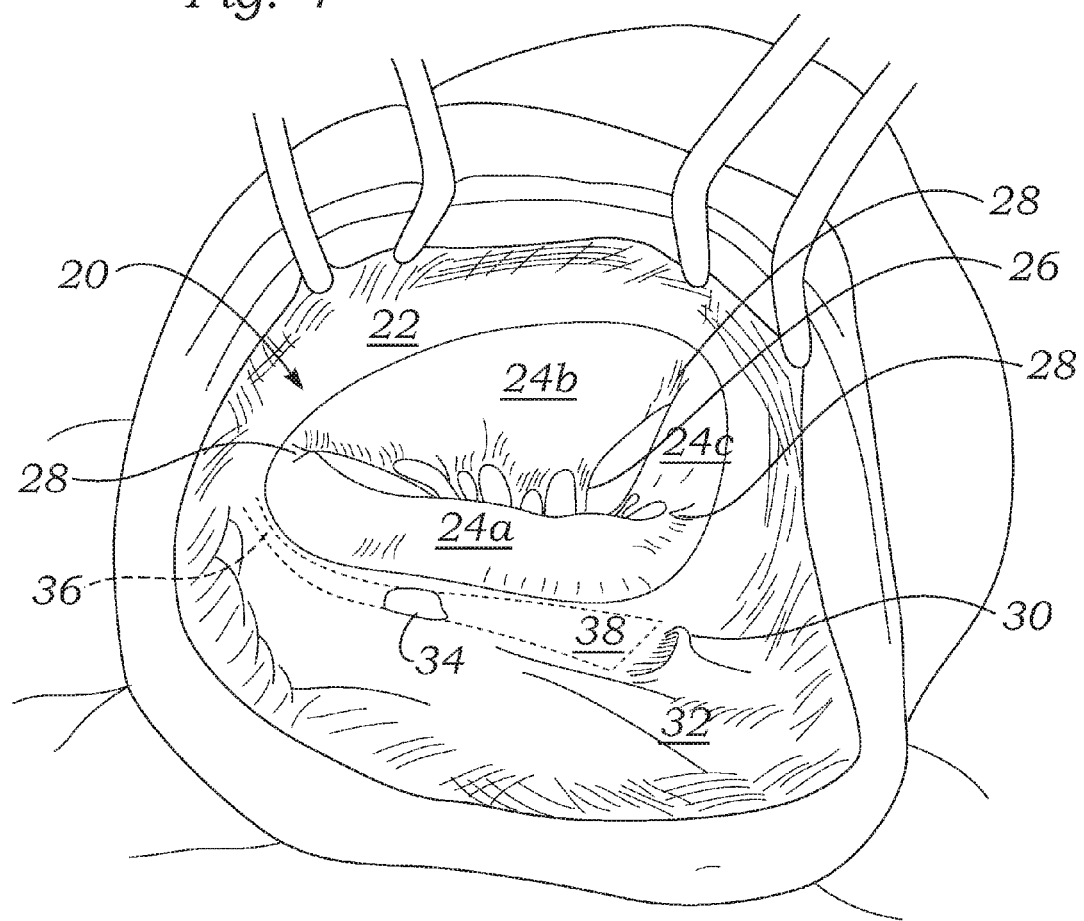
FIG. 4 is a plan view of the native tricuspid valve and surrounding anatomy from the inflow side.

The present invention provides an improved tricuspid annuloplasty ring that better conforms to the native annulus and is shaped to protect certain features of the surrounding anatomy. The exemplary ring disclosed herein supports a majority of the tricuspid annulus without risking injury to the leaflet tissue and heart's conductive system, such as the AV node 34 and bundle of His 36 (see FIG. 4). Additionally, the present ring is contoured to better approximate the three-dimensional shape of the tricuspid annulus; specifically, the ring is substantially planar but includes a bulge in the inflow direction at the location of the bulge created by the adjacent aorta. The bulge helps reduce stress between the ring and surrounding tissue, and thus the potential for tearing or ring dehiscence.

It should also be understood that certain features of the present tricuspid ring might also be applicable and beneficial to rings for other of the heart's annuluses. For instance, the present ring includes upturned or bent free ends that help reduce abrasion on the adjacent leaflets. The same structure might be used in a discontinuous ring for the mitral valve annulus.

The term "axis" in reference to the illustrated ring, and other non-circular or non-planar rings, refers to a line generally perpendicular to the ring that passes through the area centroid of the ring when viewed in plan view. "Axial" or the direction of the "axis" can also be viewed as being parallel to the direction of blood flow within the valve orifice and thus within the ring when implanted therein. Stated another way, the implanted tricuspid ring orients about a central flow axis aligned along an average direction of blood flow through the tricuspid annulus. Although the rings of the present invention are 3-dimensional, portions thereof are planar and lie perpendicular to the flow axis, as will be seen.

FIGS. 5A-5D illustrate a physiologic tricuspid ring 50 of the present invention having a waveform ring body 52 generally arranged about an axis 54 and being discontinuous so as to define two free ends 56a, 56b. The axis 54 lies at the approximate centroid of the ring or along the axis of blood flow through the ring 50 when implanted, and it will be understood that the relative directions up and down are as viewed in FIG. 5C. Using this convention, the ring 50 is designed to be implanted in a tricuspid annulus such that blood will flow in the downward direction.

As with existing rings, sizes 24 mm through 36 mm in 2 mm increments are available having outside diameters (OD) between 31.2-41.2 mm, and inside diameters (ID) between 24.3-34.3 mm. Again, these diameters are taken along the "diametric" line spanning the greatest length across the ring, as seen in plan view in FIG. 5B. It should be mentioned, however, that the present invention is not limited to the aforementioned range of sizes, and rings smaller than 24 mm or larger rings of 38 or 40 mm OD are also possible, for example. The "ring size" is the size labeled on the annuloplasty ring packaging.

Figure 1:
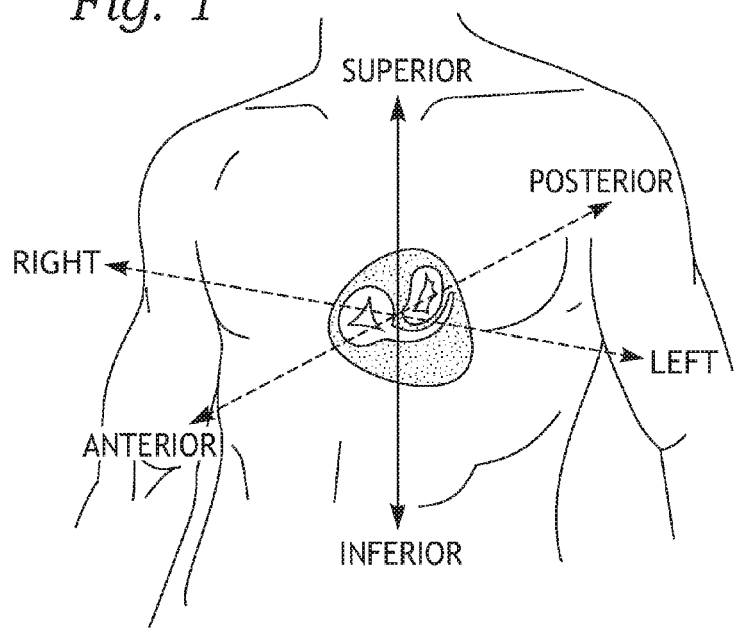
FIG. 1 is a schematic representation of the AV junctions within the heart and the body in the left anterior oblique projection.
Figure 2:
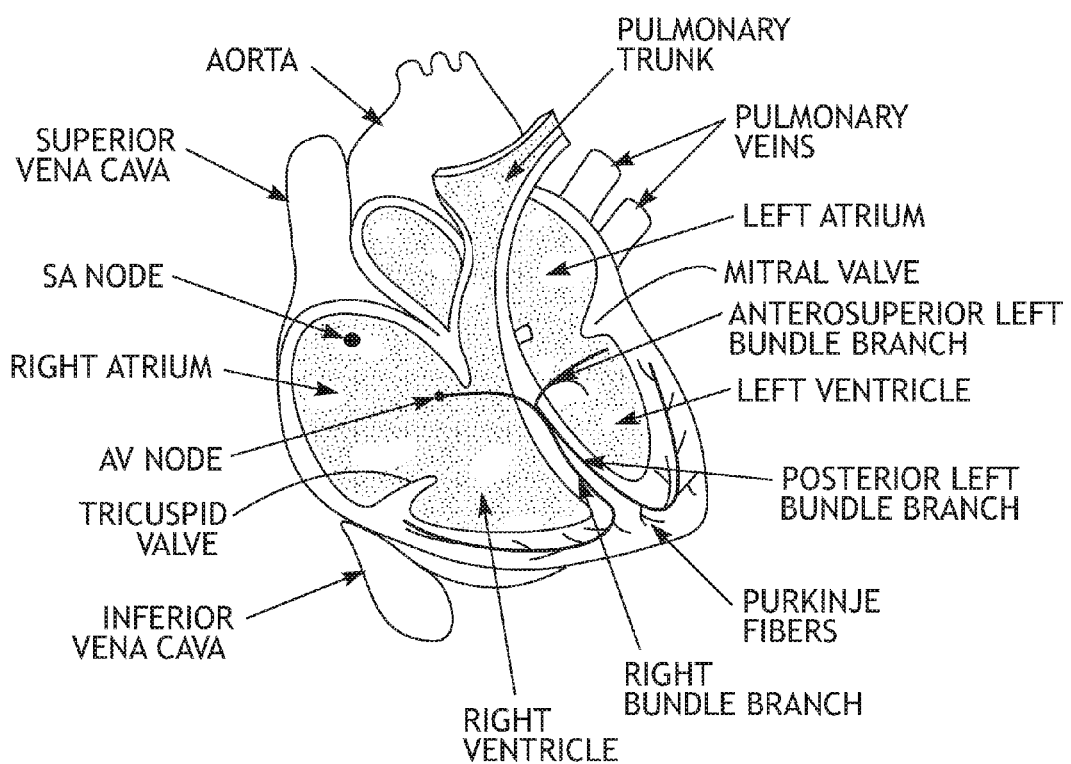
FIG. 2 is a cutaway view of the heart from the front, or anterior, perspective.
Figure 3:
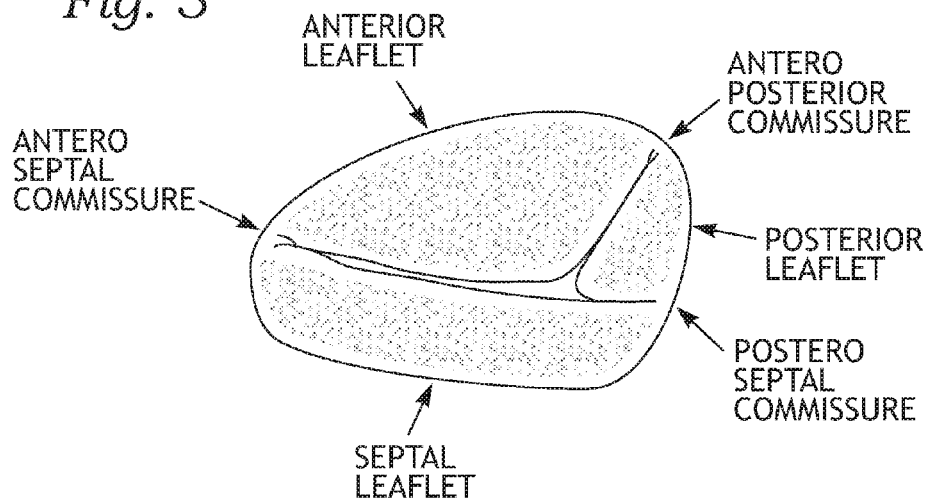
FIG. 3 is a schematic plan view of the tricuspid annulus with typical orientation directions noted as seen from the inflow side.

As seen in FIGS. 5A-5C and also in FIGS. 6A-6J, the ring body 52 is substantially asymmetric and ovoid with the first free end 56a located adjacent the antero-septal commissure when implanted (see FIG. 3). The ring body 52 extends from the first free end 56a in a clockwise direction, as seen looking at the inflow side in FIG. 5B, around a first segment 60a corresponding to the aortic part of the anterior leaflet, a second segment 60b corresponding to the remaining part of the anterior leaflet and ending at the postero septal commissure, and a third segment 60c from the postero septal commissure to the second free end 56b, which is mid-way along the septal leaflet. The nomenclature for these segments is taken from the standard anatomical nomenclature around the tricuspid annulus as seen in FIG. 3.

The precise relative dimensions of the segments may vary, but they are generally as indicated in the view of FIG. 5B. That is, the second segment 60b is the largest, followed by the first segment 60a and third segment 60c. It should be further noted that the term "asymmetric" means that there are no planes of symmetry through the ring body 52 looking from the inflow side, and "ovoid" means generally shaped like an egg with a long axis and a short axis, and one long end larger than the other. A substantial portion of the ring body 52, in particular the second segment 60b, is planar, though the first segment 60a includes an upward bulge and most of the third segment 60c dips downward.

The exemplary ring 50 features a "waveform contour" in that it extends in a three-dimensional path around its periphery that curves up and down in select locations. A mid-portion of the ring 50 is preferably planar, but both outer segments trace both up and down paths. The term "waveform" thus means an undulating or up and down path.

The free ends 56a, 56b of the exemplary ring 50 are upturned in the inflow direction so as to help reduce abrasion on the adjacent leaflets (septal, or both septal and antero-superior). The upturned free ends 56a, 56b nest in an anatomical depression in the tricuspid annulus. Prior rings that are not completely flexible terminate in ends that are typically extensions of the ring periphery, that is, they do not deviate from the paths that the adjacent segments of the ring follow. The upturned ends 56a, 56b nest in the anatomical depression and present curved surfaces that the constantly moving leaflets might repeatedly contact, as opposed to point surfaces so that forcible abrasion of the moving leaflets in contact with the ends of the ring is avoided.

As seen in FIGS. 5A and 5C, the exemplary ring 50 also includes an upward arcuate bow or bulge 64 in the first segment 60a. The "aortic" bulge 64 accommodates a similar contour of the tricuspid annulus due to the external presence of the aorta, and desirably extends from near the first free end 56a along first segment 60a to a location that corresponds to the end of the aortic part of the anterior leaflet. Prior tricuspid rings are substantially planar, and if at all rigid they necessarily deform the annulus to some extent at this location. The aortic bulge 64 helps reduce stress upon implant and concurrently reduces the chance of dehiscence, or the attaching sutures pulling out of the annulus. The axial height of the aortic bulge 64 above the nominal top surface of the ring body 52 is between about 3-9 mm, preferably about 6 mm.

Now with particular reference to FIG. 5D, the tricuspid ring 50 of the present invention is seen in sectional view to illustrate the inner construction. The ring body 52 preferably comprises an inner structural support member or core 70 encompassed by an elastomeric interface 72 and an outer fabric covering 74. The inner core 70 extends substantially around the entire periphery of the ring body 52 and is formed from a relatively rigid material such as stainless steel, titanium, and Cobalt Chromium (CoCr family of alloys: CoCr, L605, MP, MP25, MP35N, Elgiloy, FW-1058). The term "relatively rigid" refers to the ability of the core 70 to support the annulus without substantial deformation, and implies a minimum elastic strength that enables the ring to maintain its original shape after implant even though it may flex somewhat. Indeed, as will be apparent, the ring desirably possesses some flexibility around its periphery. To further elaborate, the core 70 would not be made of silicone, which easily deforms to the shape of the annulus and therefore will not necessarily maintain its original shape upon implant. Instead, the ring core 70 is preferably formed from one of the relatively rigid metals or alloys listed above, or even a polymer that exhibits similar material and mechanical properties. For instance, certain blends of Polyether ether ketone (PEEK) with carbon and an alloy might be used, in which case the core could be injection molded.

The elastomeric interface 72 may be silicone rubber molded around the core 70, or a similar expedient. The elastomeric interface 72 provides bulk to the ring for ease of handling and implant, and permits passage of sutures though not significantly adding to the anchoring function of the outer fabric covering 74. The elastomeric interface 72 has a constant wall thickness around a majority of the core 70 of about 0.25 mm, but is somewhat thicker at the free ends 76a, 76b; preferably about 0.51 mm thick. The fabric covering 74 may be any biocompatible material such as Dacron® (polyethylene terephthalate), and desirably has a thickness of about 0.33 mm.

As seen in FIG. 5D, the elastomeric interface 72 and fabric covering 74 project outwards along the outside of the ring 50 in a sewing cuff or flange 76 to provide a highly visible and accessible platform through which to pass sutures. The exemplary flange 76 projects radially outward a distance of about 1.2 mm, or roughly between ⅓ and ½ of the total radial thickness of the ring body 52. To delineate the sewing flange 76 on the underside of the ring 50, a peripheral marker 78 such as a suture line is provided. The marker 78 indicates to the surgeon the base or inner radial extent of the sewing flange 76 to facilitate passage of sutures through the ring 50. Preferably, the inflow edge of the ring body 52 and the outwardly projecting flange 76 provide a regular and smooth surface to prevent thrombus formation.

An exemplary construction of the ring body 52 is a solid titanium (or suitable alternative) core 70 extending from the first free end 56a to the second free end 56b. The core 70 possesses selective flexibility, meaning that it is more flexible in certain areas than others, and about particular axes. A particularly desirable result of any selectively flexible core is ring flexibility in torsion which allows the ring to move with the cyclic movement of the tricuspid annulus while still providing shape correction. Preferably, the exemplary ring body 52 features a waveform contour and anterior-posterior flexibility within the waveform.

FIGS. 6A-6J show further details of the exemplary inner core member 70 of the tricuspid annuloplasty ring 50. Again, a preferred material is titanium or a Ti alloy such as Ti-6Al-4V (Titanium-Aluminum-Vanadium), annealed to remove residual internal stresses. FIG. 6C indicates segments 80a, 80b, 80c around the core member 70 that correspond to the segments 60a, 60b, 60c around the assembled ring 50, as seen in FIG. 5B. With simultaneous reference to FIG. 6D just below FIG. 6C, the reader will see that the transitions between the three peripheral segments 80a, 80b, 80c generally align with the points at which the core member 70 changes from planar to nonplanar. That is, the second segment 80*b* lies in a nominal plane of the core member 70 perpendicular to the central axis, the first segment 80*a* bows upward, while the third segment 80*c* drops downward. It should be noted, however, that these general directions are modified by upturned free ends 90*a*, 90*b*, and the first and third segments thus form complex curves.

In particular, the first segment 80*a* is seen best in FIG. 6F, and includes a smooth upward bow 92 that forms a gentle arc with an apex about in the middle of the segment. As mentioned, the free end 90*a* is upturned, and a downwardly convex bend 94 separates the free end from the upward bow 92. The downwardly convex bend 94 is still raised up above the level of the planar second segment 80*b*, and thus the entire first segment 80*a* is raised above the nominal reference plane R (see FIG. 13B) of the core member 70, though in a complex curve.

The second segment 80*b* desirably lies in and defines a nominal plane of the core 70. In one embodiment, the first and third segments 80*a*, 80*c* are defined at the ends of the planar second segment 80*b*, and thus form the three-dimensional components of the core. However, it should be noted that a second upward bow (not shown) may be provided in the second segment 80*b*, at least in that portion that will be implanted adjacent the posterior leaflet of the tricuspid valve (see FIG. 3). In that configuration, the second segment 80*b* would be planar on both ends except for an upward bow in a mid-portion.

FIG. 6C illustrates radial lines (unmarked) at each free end 90*a*, 90*b* and between adjacent segments 80*a*-80*b* and 80*b*-80*c*. The core 70 in plan view is not circular and thus the term "radial" refers not to lines radiating out from a single central axis (despite the use of "central flow axis 54"), but instead to lines perpendicular to tangents through the centerline of each particular section or segment of the core 70. Angular spans between the "radial" lines can be approximated by measuring the included angle between the lines. The indicated radial lines therefore divide the core 70 into the segments 80*a*, 80*b*, 80*c* as follows: the first segment 80*a* extends around an arc of about 96°, the second segment 80*b* extends around an arc of about 113°, and the third segment 80*c* extends around an arc of about 66°. Therefore, the total angular span of the core 70 is about 275°, leaving a gap between the free ends 76*a*, 76*b* with a span of about 85°. The marked 30° angle in FIG. 6C indicates the angular span between a line drawn horizontally across the major axis and the commencement of the third segment 80*c*.

The core 70 includes regions that, in use in an implanted ring 50, experience high stress and those that experience low stress. Generally, the free ends 76*a*, 76*b* and corresponding first and third segments 80*a*, 80*c* experience low stress, while the second segment 80*b* experiences high stress. To provide adequate stiffness and fatigue life, therefore, the core cross-section is more robust in the middle second segment 80*b* than at the end segments 80*a*, 80*c*, as will be detailed below.

FIG. 6D best shows the third segment 90*c*, which descends downward from the second segment 80*b* to a lower apex 100, which is downwardly convex. The second free end 90*b* then angles upward again, but does not reach the level of the planar second segment 80*b*. Thus, the entire third segment 80*c* is lowered below the nominal plane of the core member 70, or at least below the planar second segment 80*b*, though again in a complex curve.

The core member 70 preferably has a cross-section that renders the ring 50 highly flexible in torsion, while maintaining a relatively stiff radial bending profile. A number of different cross-sections may be used to this effect, as will be described below. Furthermore, the core member 70 cross-section provides selective flexibility so that portions are more flexible than others about various axes. More detail and alternatives in this regard will be provided below, though in a preferred configuration the core member 70 has greater flexibility in up-and-down bending adjacent the free ends 90*a*, 90*b* than in its mid-section, such as in the second segment 80*b*.

In general, the prosthetic tricuspid annuloplasty rings disclosed herein each comprise a ring body surrounding a vertical axis along an inflow-outflow direction and a radial plane perpendicular thereto. A first free end and a second free end are separated across a gap and the ring body extends at least half-way around the vertical axis. The ring body includes an inner core member such as core member 70 that has an "in-plane bending stiffness" in a plane perpendicular to the vertical axis measured by moving one free end radially with respect to the other free end that is at least 10 times the torsional out-of-plane bending stiffness measured by moving one free end vertically with respect to the other free end. Preferably the core member has an in-plane bending stiffness that is between about 10-200 times the torsional out-of-plane bending stiffness, more preferably between about 20-60 times the torsional out-of-plane bending stiffness, and most desirably between about 20-40 times the torsional out-of-plane bending stiffness. For further explanation of these axes see the "out-of-plane" bending axis $z_c$ and "in-plane" bending axis $y_c$ through the section shown in FIG. 13D.

In a particularly desirable configuration, the core member 70 has a U-shaped cross-section open in the inflow direction (up in FIG. 6D) around substantially its entire periphery, except at the two free ends 90*a*, 90*b* which each include an end wall that closes the U-shape. FIG. 6H is a radial cross-section through a section of the second segment 80*b* and illustrates the U-shape, with a lower floor 102, an inner wall 104, and an outer wall 106. In a preferred configuration the U-shape exhibits symmetry about a vertical mid-line such that the inner wall 104 and outer wall 106 are identical, though they may differ, such as having different heights. Lower corners 108 are shown chamfered at about 45° angles, though they may also be rounded without significant change in physical properties. The chamfered corners 108 are easier to form through machining, for example. Chamfered or rounded corners 108 help reduce the torsional stiffness in the core cross-section and create a facsimile of a constant wall thickness around the "U-shape." In a preferred manufacturing process, the waveform, U-shaped cross-section core 70 is machined directly from bar stock, though it may also be formed flat and then bent to the waveform shape. In the latter case, annealing may be required to remove residual material stresses.

The second segment 80*b* preferably has a varying cross-section along its length, with the section seen in FIG. 6H as well as a second section seen in FIG. 6I both extending in a constant manner for a short distance. The second section seen in FIG. 6I is also U-shaped but has relatively thinner walls 102', 104', 106' than the section in FIG. 6H. In other words, the section shown in FIG. 6H is stiffer than the section in FIG. 6I. A still further radial section through the third segment 80*c* is seen in FIG. 6J, and illustrates reduced height inner and outer walls 104", 106'. The thinner core member 70 near the free ends 90*a*, 90*b* flexes more easily in the vertical direction. The sections of constant cross-section desirably extend around the core 70 along a certain length or span, which is described below and shown in FIG. 13A.

FIGS. 7A-7C are different perspective views of a ring holder 120 for delivering the tricuspid annuloplasty ring 50 of FIG. 5A to a tricuspid annulus for implant. As mentioned, the core member 70 is a relatively rigid material that resists deformation, even if it may flex to a certain degree when implanted. As such, the ring holder 120 includes a template 122 with a peripheral mounting ring 124 that conforms to the three-dimensional shape of the ring 50 and likewise terminates in free ends. On the left side of FIG. 7A the mounting ring 124 is seen as having a generally vertical inner wall 130 intersecting a generally horizontal upper wall 132, together which define an approximately right-angle groove or channel for receiving the annuloplasty ring 50. The annuloplasty ring 50 attaches to the mounting ring 124 using one or more sutures that pass through apertures 134 in the upper wall 132 and through the suture-permeable portions of the annuloplasty ring. A single cutting guide 136 provides a convenient location at which to sever the attaching sutures and release the annuloplasty ring 50 from the mounting ring 124, as will be further explained below.

The template 122 further includes a number of spokes 140, three as illustrated, that connect the peripheral channel 124 to a central hub 142. The spaces between the spokes 140 and within the mounting ring 124 enhance visibility of the distal end of the assembly to help the surgeon visualize the tricuspid annulus and guide the annuloplasty ring 50 into place. The holder 120 also preferably includes a plurality of radiopaque markers embedded or otherwise provided thereon for X-ray visualization. For instance, markers in the central hub 142 may be included, or around the periphery of the mounting ring 124 or just at the free ends of the mounting ring. The hub 142 projects upward as a post and terminates at bifurcated fingers 144 that form part of a resilient latching arrangement for mating with a delivery handle.

As mentioned, the mounting ring 124 mimics the three-dimension shape of the annuloplasty ring 50 so that the ring is held in close contact with the channel defined thereby. The mounting ring 124 thus include a planar portion 146 in which is positioned the cutting guide 136 and corresponding to the planar second segment 60b of the ring 50 as seen in FIG. 5B. FIG. 7D is an orthogonal view with the planar portion 146 oriented horizontally to illustrate the angle θ from the vertical at which the central hub 142 extends upward. This angular arrangement facilitates delivery of the ring 50 by permitting the surgeon to advance the ring holder 120 and seat the ring 50 without the visual impediment of a handle that projects straight upward.

FIG. 8A shows exploded the tricuspid annuloplasty ring 50, ring holder 120, and a delivery handle 150 that attaches to the holder. The handle 150 has a proximal grip 152, a middle malleable rod 154, and a distal connector 156 that mates with the bifurcated fingers 144 of the holder hub 142. The assembly of the ring 50 and holder 120 is shown disconnected from the handle 150 in FIG. 8B. The connection between the handle 150 and holder 120 may be a simple friction fit, which can be overcome by pulling both elements away from one another, or may involve a latching mechanism that requires pressing a button or slider (not shown). In either case, detachment of the handle 150 from the holder 120 is relatively simple.

FIGS. 9-12 illustrate several steps in the implant procedure, as will be explained.

First, the surgeon utilizes valve annulus sizers to measure the tricuspid valve for annuloplasty ring size. Typical sizing technique for tricuspid valve annuloplasty includes assessment of septal leaflet length using two notches on a plate-like sizer (such as Tricuspid Sizers available from Edwards Lifesciences of Irvine, Calif.), and evaluation of anterior leaflet surface area. The surgeon should not attempt to deform or alter the ring 50 to conform to a specific annular anatomy, as it could damage the ring. Instead, if the ring 50 is not suitably sized for the annulus, a larger or smaller ring should be selected.

Ultimately, the surgeon determines the proper size of ring, and the assembly of tricuspid annuloplasty ring 50 and ring holder 120 is provided to the operating room. The tricuspid annuloplasty ring 50 is supplied in a sterile package with the ring holder 120 in the configuration of FIG. 8B. The procedure for gaining access to the tricuspid annulus involves performing a sternotomy and then stopping the heart and placing the patient on bypass. The tricuspid annulus is exposed through the right atrium. Further details on the surgical steps surrounding the tricuspid repair are well known to the surgeon.

Next, the surgeon or surgeon's assistant attaches the handle 152 to the holder 120 in a one-step motion by snapping the handle into the engaging component on the holder as shown in FIG. 8B.

FIG. 9 shows one of a plurality of suture needles 160 passing through the annuloplasty ring 50. The surgeon uses the needles 160 to pre-install a plurality of implant sutures 162 using horizontal mattress stitches around the annulus, and thread them through corresponding locations around the ring 50. No sutures 162 are placed in the atrial tissue or through the area of the Bundle of His, which may impair cardiac conduction, nor through the right coronary artery. This is a typical implant technique for both annuloplasty rings and prosthetic heart valves and is followed by sliding or "parachuting" the ring 50 down the array of pre-installed sutures 162 into contact with the annulus. The holder template 122 includes the windows between the spokes 140 (FIG. 7C) that allow visualization of the tricuspid valve and annulus during parachuting. In addition, the central hub 142 angles toward the anterior portion of the ring as seen in FIG. 7D to further assist with visualization. Note that prior to the surgery the annulus is distended such that the valve leaflets do not fully coapt or come together and thus permit regurgitation.

FIGS. 10 and 10B are radial cross-sections through the tricuspid annuloplasty ring 50 showing proper and improper suture needle threading techniques. The proper method shown in FIG. 10A is to pass the suture needle 160 directly through the sewing flange 76 of the ring body 52, and preferably as close to the base of the sewing flange as possible. In this way, the needles 160 and trailing sutures 162 pass through a thicker portion of the silicone interface 72 to minimize the chance of pulling out after implant. To help the surgeon aim the needle 160, the physiologic tricuspid ring 50 includes a peripheral marker line 78 under the sewing flange 76, and in particular at the corner at the base of the flange. The marker line 78 extends around and on the outflow side of the ring body 52 substantially from one free end 56a to the other 56b. In one embodiment, the marker line 78 comprises one or more colored sutures, such as an interrupted or dashed line formed by a single suture passed in and out of the ring body 52. The marker line 78 provides a clear visual indicator for the surgeon to aim for, and delineates the base of the sewing flange 76 below which the needle 160 should not be passed.

On the other hand, FIG. 10B shows a suture needle 160 having been passed below the marker line 78 toward the inner solid core member 70. If this occurs, the surgeon will encounter solid resistance to further passage, and can retract the needle and try again. However, the shape of the core member 70 is such that an occasional missed needle pass may not be a problem. That is, the core member 70 has the U-shape that deflects as opposed to catching the needle 160. The lower corners are either chamfered or rounded so that the needle 160 may simply glance off and continue up through the soft interface 72. A number of previous annuloplasty rings included inner steps or separate elements around which the needle could potentially catch, which could result in an improper attachment stitch affecting the performance of the ring. The present ring 50 eliminates such problems.

After parachuting the ring 50 down the array of pre-installed sutures 162 into contact with the tricuspid annulus, the implant sutures 162 are tied off using knots 164 or possibly clips (not shown) that eliminate the time-consuming knot-tying. To increase visibility for this step, the handle 150 may first be detached from the holder 120. Finally, when surgeon has secured the ring 50 to the annulus with the sutures 162, he/she severs an attachment suture 170 connecting the ring to the holder 120. Specifically, the surgeon uses a sharp implement such as a scalpel 172 to sever the attachment suture 170 at the single cutting guide 136. Although not show in detail, the attachment suture 170 passes in and out of the ring body 52 through the apertures 134 in the upper wall 132 of the holder template 122, as seen FIGS. 7A-7C, and ties off at each end to the template. Severing the suture 170 in the middle at the cutting guide 136 permits the surgeon to simply pull the holder 10 free from the ring. The attachment suture 170 pulls out of the ring 50 at the same time.

Finally, FIG. 12 shows the tricuspid annuloplasty ring 50 fully implanted at the tricuspid annulus, with the implant sutures 162 and knots 164 holding it in place. The annulus is reshaped such that the valve leaflets coapt and prevent regurgitation.

The surgeon and his/her team then evaluates the quality of the repair by transesophageal echocardiography (TEE) after completion of cardiopulmonary bypass. Care in the measurement of the orifice, annuloplasty ring selection, and insertion technique are essential in achieving a good result. However, associated subvalvular lesions may necessitate additional procedures. If careful application of the annuloplasty ring 50 fails to produce adequate repair of valvular insufficiency as determined by echocardiography, visual inspection, or intra-operative testing, the surgeon may ultimately remove the ring 50 and replace the diseased valve with a prosthetic valve during the same procedure.

To further understand the advantageous contours and cross-sections of the physiologic tricuspid annuloplasty ring 50, FIGS. 13A-13F illustrate again the inner core member 70 with a number of key dimensions added. These dimensions will be explained below followed by exemplary values in tabular form.

Looking at the plan view of FIG. 13A, the nominal size of each ring 50 typically corresponds to a dimension A extending across the largest span of the core member 70 from one inner edge to another. That measurement is taken in a plane in which lies a major axis, if you will, of the generally ovoid-shaped ring. That is, a Size 24 ring will have a dimension A of 24 mm, and so on. The dimension Z extends across the same plane of the ring but measures the core member 70 from one outer edge to another, thus including the radial thickness of the core member on each side. Likewise, a minor axis extends perpendicularly to the major axis and the dimensions B and U indicate the distance across the inner and outer edges, respectively.

The gap between the free ends of the core member 70 has a dimension C. To help avoid interfering with the heart's conduction system adjacent the tricuspid annulus, the gap C is somewhat larger than previous rings. In a preferred embodiment, the gap C is about 48% of the nominal size of each ring. Therefore, a Size 24 ring would have a gap between the free ends of the inner core member 70 of about 11.5 mm.

The plan view shape seen in FIG. 13A exhibits a plurality of curvatures around the core member 70. Various radii having different centers are indicated at E, F, and H. In general, first segment 80a has a curve with radius E blending into a curve with larger radius F. Second segment 80b starts in a curve with radius F and blends into a curve with radius H. Third segment 80c starts in a curve with radius H and eventually straightens out at the septal free end 90b. The radius E and H are similar, with H being slightly larger. The section adjacent to the septal end 90b (bottom of ring) becomes straight, which mirrors the shape of the septal aspect of the tricuspid annulus.

The vertical heights of the various segments 80a, 80b, 80c and free ends 90a, 90b are shown in FIGS. 13B and 13C. The first segment 80a includes the upward bow 92 that rises to a height T as indicated in FIG. 13C. Height L shows the dimension to the top of the core member 70 at bow 92. Although shown in detail below in Table I, the height T above the nominal reference plane R of the core member 70 (or the upward rise of bow 92) is between about 2.0-2.9 mm. Again, the first free end 90a angles upward as shown.

The downward angle $\alpha$ of the septal segment 80c is between about 10-30°. The upturned second free end 90b makes an angle $\beta$ with the septal segment 80c, and $\beta > \alpha$, in particular $\beta \cong 2\alpha$. The septal segment 80c descends below the nominal reference plane R to a distance S. In comparison with the first segment 80a, the third segment 80c dips down a greater distance below the nominal reference plane R, and in particular S>T. The lengths of the upturned free ends 90a, 90b as shown at dimension P in FIG. 13B may differ, but preferably are the same and between about 1-2 mm, more preferably about 1.5 mm.

The following table provides exemplary dimensions for the variables shown in FIGS. 13A-13F, and as described above. These data are for ring sizes from 24-36. All dimensions are in mm.

TABLE I

Exemplary Core Member Dimensions

| Ring size (mm) | A (mm) | B (mm) | C (mm) | T (mm) | S (mm) |
|---|---|---|---|---|---|
| 24 | 24.0 | 16.6 | 11.5 | 2.0 | 2.5 |
| 26 | 26.0 | 17.9 | 12.5 | 2.2 | 2.6 |
| 28 | 28.0 | 19.3 | 13.4 | 2.3 | 2.8 |
| 30 | 30.0 | 20.7 | 14.3 | 2.5 | 2.9 |
| 32 | 32.0 | 22.1 | 15.2 | 2.6 | 3.0 |
| 34 | 34.0 | 23.5 | 16.2 | 2.8 | 3.2 |
| 36 | 36.0 | 24.8 | 17.1 | 2.9 | 3.3 |

One particularly effective feature of the present annuloplasty ring 50 is its enhanced flexibility in torsion. Instead of having a solid bar construction, or being formed with a plurality of circumferentially-stacked bands, both of which tended to be relatively stiff in torsion, the cross-section permits a great degree of torsional stress while still providing adequate circumferential stiffness for remodeling the tricuspid annulus.

As mentioned, the preferred cross-section is a U-shape as seen in FIGS. 13D-F. FIGS. 13D and 13E are taken through the second segment 80b, while 13F is taken through the third segment 80c. It should be noted that the cross-sections at the free ends are substantially equivalent, so that section 13F-13F could also be taken near the first free end 90a.

FIG. 13A shows a number of spans around the periphery of the core 70 that illustrate sections of constant cross-section. The exemplary core 70 includes four sections of constant cross-section between which are transition regions. Adjacent sections of constant cross-section have at least one dimensional difference, and the transition regions provide generally linearly or smoothly changing dimensions therebetween. The sections seen in FIGS. 13D-13F correspond to those shown in FIGS. 6H-6J. In general, the cross-sections around the core 70 vary to provide more flexibility in certain areas while stiffening other areas that experience greater stresses in use.

Though there are four sections of constant cross-section, two of the sections at the free ends of the core 70 are preferably identical, and thus FIG. 13F represents the cross-section at both free ends 76a, 76b. The corresponding spans over which the constant free end sections extend are shown in FIG. 13A.

The stiffest core section as seen in FIG. 13D extends around span 13D-13D wholly within the second segment 80b. Span 13D-13D is also the longest of the three constant cross-section spans, and extends between about 60-70°. The next stiffest core section as seen in FIG. 13E extends around span 13E-13E, also wholly within the second segment 80b. Span 13E-13E is the shortest and has an angular extent of between about 30-40°. The first segment 80a includes the constant cross-section seen in FIG. 13F, which is preferably the same as in the third segment 80c, both shown by spans 13F-13F. It should be noted that the span 13F-13F in the first segment 80a is somewhat longer than that in the third segment 80c. In one embodiment, the span 13F-13F in the first segment 80a extends between about 55-65°, while the span 13F-13F in the third segment 80c extends between about 20-30°. Though the cross-sections in the first and third segments 80a, 80c are preferably the same (as seen in FIG. 13F), and the most flexible around the core 70, they may also be different with the section in the septal third segment 80c preferably being the most flexible.

FIG. 13D also shows two bending axes through that particular section. A torsional "out-of-plane" bending axis $z_c$ through the section centroid represents the local axis about which the core member 70 twists when its two free ends 76a, 76b are displaced vertically with respect to one another (or one is held fixed while the other moves vertically). An "in-plane" bending axis $y_c$ through the section centroid represents the local axis about which the core member 70 bends when its two free ends 76a, 76b are displaced radially with respect to one another.

Specific dimensions for the constant cross-section spans as called out in FIGS. 13D-13F will now be discussed and exemplary values are provided in Table II below.

Some trends from Table II are evident. In the exemplary embodiment, the width w of the core member 70 remains the same around its periphery, while the height changes. So, the widths $w_D$, $w_E$ and $w_F$ shown in FIGS. 13D-13F, respectively, are preferably equal (as reflected in the single column in Table II for dimension w), though they get wider for larger ring sizes. On the other hand, the heights $h_D$ and $h_E$ as seen in FIGS. 13D and 13E, respectively, are taller than the height $h_F$ in FIG. 13F. Indeed, the heights $h_D$ and $h_E$ as seen in FIGS. 13D and 13E are preferably equal such that the height around the second segment 80b remains constant. FIGS. 13B and 13C show the transitions between the taller mid-portion of the ring and the shorter end segments, and in particular illustrate short transitions 96 over which the height of the core member 70 gradually ramps down from $h_D$ and $h_E$ to $h_F$. As illustrated, the shorter height $h_F$ remains constant to the free ends 90a, 90b, though this dimension could also change. The shorter free end portions permit greater flexing in the vertical plane than the mid-portions of the core member 70.

The thickness of the side walls and the thickness of the web or floor of the preferred U-shape may remain constant around the core periphery or may taper as well. Desirably, the wall and floor thicknesses vary between zones of low stress and high stress to maximize flexibility in torsion yet retain good fatigue strength. For instance, the wall and floor thicknesses may be reduced toward the free ends 76a, 76b of the core 70, or perhaps in the first and third segments 80a, 80c, which ends tend to experience less stresses from relative up and down movement of the annulus at those locations. In other words, the higher torsional stresses occur in the middle of the core 70. Any change in thickness dimensions is desirably gradual to avoid steps and accompanying stress concentrations.

Table II above includes exemplary dimensions for the core cross-section in the middle and end regions. Preferably, the thickness of the side walls of the all of the cross-sections is less than the thickness of the floor of the same section. For instance, the thickness $t_{1D}$ of the side walls of the stiffest cross-section seen in FIG. 13D is less than the thickness $t_{2D}$ of the floor of the same section. Furthermore, the thicknesses of the side walls and floor $t_{1D}$, $t_{2D}$ of the stiffest cross-section seen in FIG. 13D are desirably greater than that ($t_E$) in the second most stiffest section shown in FIG. 13E and in the most flexible section ($t_F$) shown in FIG. 13F. However, in one embodiment the thicknesses of the side walls and floor ($t_E$) of the moderately stiff section shown in FIG. 13E are desirably the same as that ($t_F$) in the most flexible section shown in FIG. 13F.

At this stage it is important to understand the particular physical characteristics of the core member 70 to fully grasp the improved physiologic match with the tricuspid annulus.

TABLE II

Exemplary Core Member Cross-Sectional Dimensions

| Ring size (mm) | w (mm) | $h_D$ (mm) | $h_E$ (mm) | $h_F$ (mm) | $t_{1D}$ (mm) | $t_{2D}$ (mm) | $t_E$ (mm) | $t_F$ (mm) |
|---|---|---|---|---|---|---|---|---|
| 24 | 1.83-1.93 | 1.27-1.37 | 1.27-1.37 | 0.76-0.86 | 0.33-0.41 | 0.43-0.51 | 0.25-0.36 | 0.25-0.36 |
| 26 | 1.91- | 1.27-1.37 | 1.27-1.37 | 0.76-0.86 | 0.33-0.41 | 0.43-0.51 | 0.25-0.36 | 0.25-0.36 |
| 28 | 2.00-2.10 | 1.27-1.37 | 1.27-1.37 | 0.76-0.86 | 0.33-0.41 | 0.43-0.51 | 0.25-0.36 | 0.25-0.36 |
| 30 | 2.08-2.18 | 1.27-1.37 | 1.27-1.37 | 0.76-0.86 | 0.33-0.41 | 0.43-0.51 | 0.25-0.36 | 0.25-0.36 |
| 32 | 2.16-2.26 | 1.27-1.37 | 1.27-1.37 | 0.76-0.86 | 0.33-0.41 | 0.43-0.51 | 0.25-0.36 | 0.25-0.36 |
| 34 | 2.24-2.34 | 1.27-1.37 | 1.27-1.37 | 0.76-0.86 | 0.33-0.41 | 0.43-0.51 | 0.25-0.36 | 0.25-0.36 |
| 36 | 2.29-2.39 | 1.27-1.37 | 1.27-1.37 | 0.76-0.86 | 0.33-0.41 | 0.43-0.51 | 0.25-0.36 | 0.25-0.36 |

In general, the physical characteristics of the ring 50 are determined by those of the core member 70. The ring 50 is both relatively stiff in the radial direction and in the vertical direction in its mid-section, but more flexible at the free ends and extremely flexible in torsion.

Figure 15:
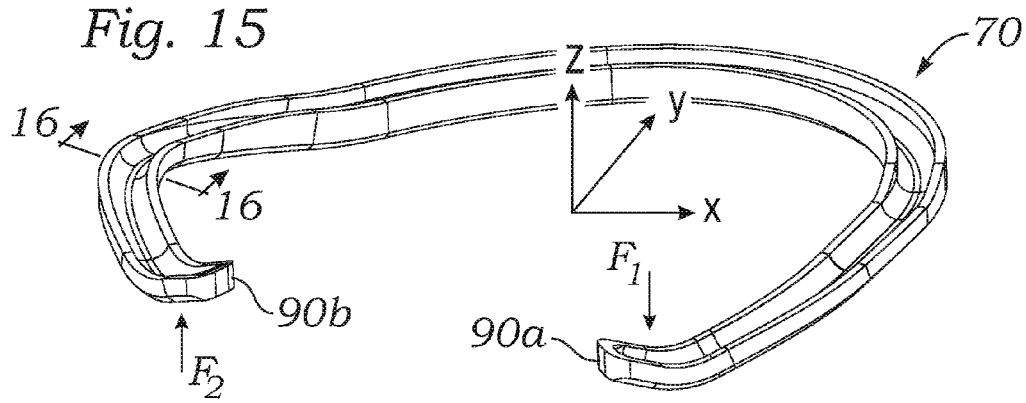
FIG. 15 is an upper perspective view of an exemplary inner core member for the tricuspid ring disclosed herein.
Figure 16A:
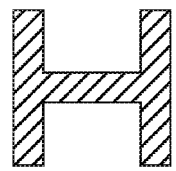
FIGS. 16A-16L are radial cross-sections of alternative inner core members for use in the tricuspid ring disclosed herein.
Figure 16B:
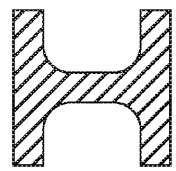
Figure 16C:
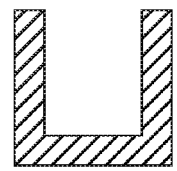
Figure 16D:
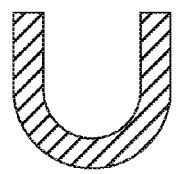
Figure 16E:
Figure 16F:
Figure 16G:
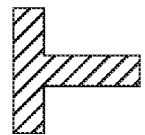
Figure 16H:
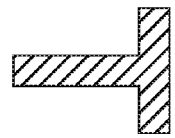
Figure 16I:
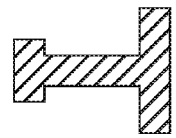
Figure 16J:
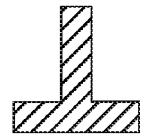
Figure 16K:
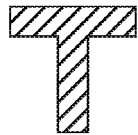
Figure 16L:
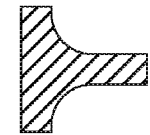

Reference is made to the orthogonal axes shown in FIG. 15. The Z- or vertical axis parallels the aforementioned central flow axis 54, while the X- and Y-axes lie in the nominal plane of the ring, perpendicular to the flow axis. Radial lines can be drawn from the Z-axis in the X-Y plane.

The core member 70 exhibits a significant resistance to bending about the Z-axis; or in other words has substantial radial stiffness. This characteristic enables the ring 50 to remodel the circumference, and typically reduce a distended annulus.

The mid-section of the core member 70 exhibits a significant resistance to bending about axes drawn along radial lines in the X-Y plane; or in other words has substantial vertical stiffness. This characteristic enables the middle of the ring 50 to resist bending about radial axes.

The free ends 90a, 90b of the core member 70 exhibits lessened resistance to bending about axes drawn along radial lines in the X-Y plane. This enables the free ends 90a, 90b to flex about radial axes.

Finally, the core member 70 is relatively flexible in torsion along its length. The axes about which the core member 70 bends in torsion are drawn through and along the core member, around the periphery thereof. Flexibility in torsion allows the core member 70 to twist about its own length when different points are subjected to opposing vertical forces, such as the forces $F_1$ and $F_2$ in FIG. 15. This characteristic permits the ring 50 to move more naturally, physiologically, if you will, with the natural rhythmic movement of the tricuspid annulus.

Figure 14:
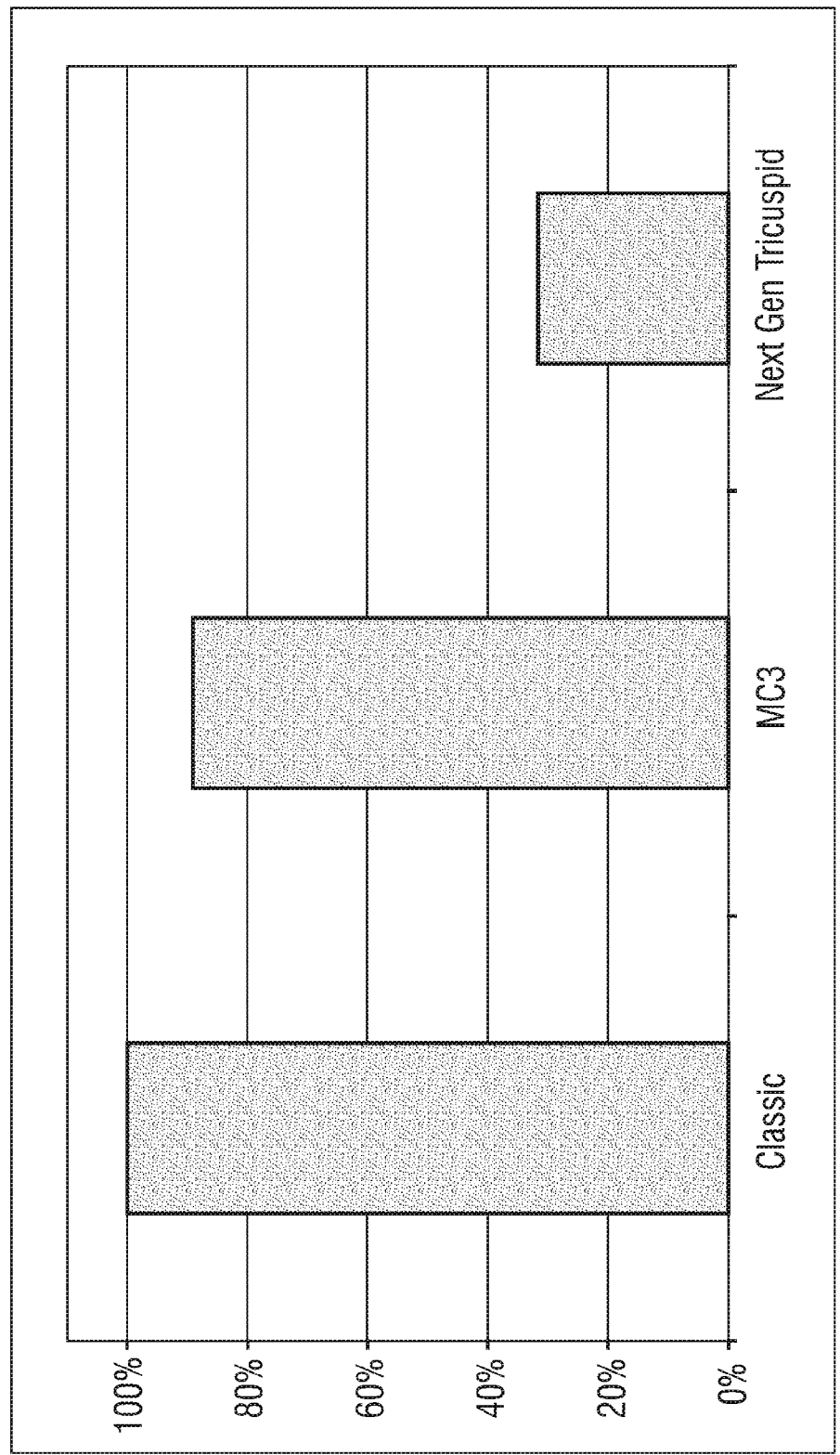
FIG. 14 is a graph showing the stiffness response to bending of a number of different tricuspid annuloplasty rings and constructions in comparison to the exemplary ring of the present application.

FIG. 14 is a graph showing the stiffness response to bending of a number of different types of core members from tricuspid annuloplasty rings in comparison to the exemplary core member 70 of the present application, denoted "Next Gen Tricuspid." The test setup involved a clamp at the septal end (septal clamp), in place of force $F_2$ in FIG. 15, and a downward force $F_1$ applied by a point load at 2.5 mm from the free end 90a. A number of loadings at varying magnitudes were performed for each ring core, and the peak load (gf) was measured and the slope of the deflection curve (gf/mm) calculated. A similar test was performed with the clamp reversed to replace force $F_1$ in FIG. 15 (anterior clamp), and a downward force was applied by a point load at 2.5 mm from the free end 90b. In each case, three (3) repeated measurements on each ring core was done, and the core member was removed from the fixture and re-installed for each measurement. Finally, tests were done on a number of different sized core members for each type. A dimensionless average of the slope lines (gf/mm) for the measured deflection curves for each were entered onto the bar graph of FIG. 14, with the stiffest ring (Classic) scaled to 100%.

Results for the exemplary core member 70 are seen on the far right, and the slope of the mass applied versus deflection is the smallest of the three types of core members. That is, less gram force (gf) was necessary to effect a given mm deflection, or in other words the core member 70 was the most flexible in torsion of the three core types.

The other two core types include: 1) solid titanium core members from the Carpentier-Edwards Classic® Tricuspid Annuloplasty Ring sold by Edwards Lifesciences Corporation of Irvine, Calif.; and 2) solid titanium core members from the Edwards MC³ Annuloplasty System™, also available from Edwards Lifesciences. The Classic® ring was the stiffest, and the MC³ ring was the next stiffest, demonstrating more than 80% of the stiffness of the Classic® ring. The Next Gen Tricuspid, or core member 70 of the present application, tested at less than 40% of the torsional stiffness of Classic® ring, and less than half that of the MC³ ring. It should be noted that the core member construction of the MC³ ring was disclosed in U.S. Pat. No. 7,367,991 to McCarthy, et al.

FIGS. 16A-16L are radial cross-sections of alternative inner core members 70 for use in the tricuspid ring 50. These cross-sections may not be as desirable as the U-shaped cross-section illustrated above, but could be substituted for reasons such as reduced profile, greater torsional flexibility, manufacturing considerations, etc. In general, any cross-section substituted should have the requisite radial stiffness in combination with torsional flexibility. The cross-sections may be described as: 16A—H-shaped; 16B—rounded H-shaped; 16C—angular U-shaped; 16D—horseshoe magnet-shaped; 16E—bowl-shaped; 16F—rounded U-shaped; 16G—left T-shape; 16H—right T-shaped; 16I—right T-shaped with flange; 16J—inverted T-shaped; 16K—T-shaped; 16L—left rounded T-shaped.

For any cross-section, the stiffness in bending about an axis starts with a calculation of the area Moment Of Inertia of the cross-section, which measures the ability of that section to resist bending. The larger the Moment Of Inertia the less the solid will bend. The smallest moment of inertia about any axis passes through the centroid (center of mass). Furthermore, the Parallel Axis Theorem can be used to determine the moment of an object about any axis, given the moment of inertia of the object about the parallel axis through the object's centroid and the perpendicular distance between the axes.

Often it is easier to compute the Moment Of Inertia for an item as a combination of pieces, the second moment of area is calculated by applying the parallel axis theorem to each piece and adding the terms. For instance, an I-beam can be analyzed as either three pieces added together or as a large piece with two pieces removed from it. Either of these methods will require use of the formula for composite cross section.

The Polar Area Moment Of Inertia of a solid's cross-sectional area measures the solid's ability to resist torsion. The larger the Polar Moment of Inertia the less the beam will twist. For a given solid, the Moment Of Inertia about two orthogonal axes through the centroid can be calculated, and then the Polar Area Moment Of Inertia is the sum of those two moments.

Figure 17:
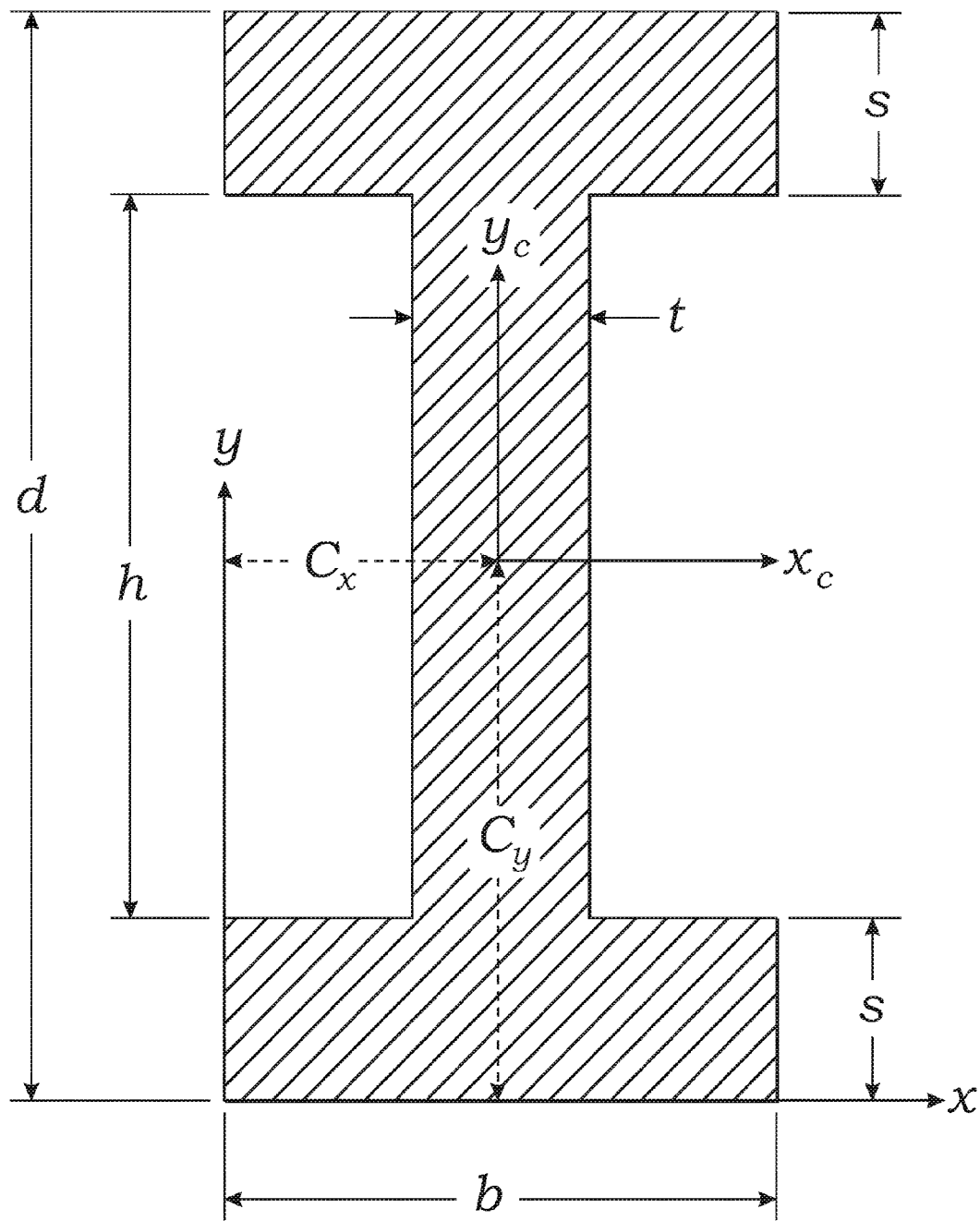
FIG. 17 is a geometric representation of an I-beam indicating dimensions and axes for purpose of calculating bending moments of inertia.

As an example, for an I-beam shown in FIG. 17, the two Moments of Inertia and Polar Moment are calculated below:

| Moment of Inertia about the $x_c$ axis | Moment of Inertia about the $y_c$ axis | Polar Moment of Inertia about the $z_c$ axis |
|---|---|---|
| $I_{xc}$ $$\frac{bd^3 - h^3(b-t)}{12}$$ | $I_{yc}$ $$\frac{2sb^3 + ht^3}{12}$$ | $= I_{xc} + I_{yc}$ |

These mathematical formulae can be used to calculate the torsional stiffness for any of the exemplary cross-sections of the core member 70 disclosed herein. For comparison purpose, the overall dimensions w and $h_1$ from FIG. 13D can be used for the outside dimensions of any of the alternatives in FIGS. 16A-16L.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. A prosthetic tricuspid annuloplasty ring, comprising:
an asymmetric generally ovoid ring body having an inflow side and an outflow side with a first free end located adjacent an antero-septal commissure when implanted and a second free end located at a septal point, wherein the ring body extends in a clockwise direction as seen looking at the inflow side from the first free end around a first segment, a second segment, and a third segment that terminates in the second free end, and the ring body includes a relatively rigid inner core member and a suture-permeable interface surrounding the inner core member, wherein the inner core member, in the second segment, has a U-shaped radial cross-section open toward the inflow side with a first height $h_1$ and which, in the first and third segments, also has a U-shaped cross-section open toward the inflow side with lesser heights relative to $h_1$.

2. The tricuspid annuloplasty ring of claim 1, wherein the suture-permeable interface includes an outwardly projecting flange on an inflow edge of the ring body and an outer fabric cover, and the ring further includes a visible marker line on the fabric cover at the base of the flange on its outflow side.

3. The tricuspid annuloplasty ring of claim 1, wherein the core member includes gradual transitions between the U-shaped radial cross-section of the first height $h_1$ and the U-shaped cross-sections of lesser heights.

4. The tricuspid annuloplasty ring of claim 1, wherein at any one point around the core member the U-shaped radial cross-sections include side walls having a thickness $t_1$ and a web having a thickness $t_2$, and wherein the thicknesses $t_1$ and $t_2$ vary gradually around the core member to provide optimal flexibility.

5. The tricuspid annuloplasty ring of claim 4, wherein the thicknesses $t_1$ and $t_2$ taper down from the second segment to both the first and third segments.

6. The tricuspid annuloplasty ring of claim 1, wherein the core member has an in-plane bending stiffness measured by moving one free end in the radial plane with respect to the other free end that is at least 10 times the torsional out-of-plane bending stiffness measured by moving one free end vertically with respect to the other free end.

7. The tricuspid annuloplasty ring of claim 1, wherein the second segment is generally planar with the first segment rising up therefrom in a complex curve and the third segment descending down therefrom in a complex curve.

8. The tricuspid annuloplasty ring of claim 7, wherein the complex curves in both the first and third segments terminate in upturned free ends.

9. A prosthetic tricuspid annuloplasty ring, comprising:
a ring body circumscribing a central area and having an inflow side and an outflow side facing in opposite directions, a portion of the ring body being generally planar so as to define a radial plane, with a first free end and a second free end separated across a gap and the ring body extends at least half-way around the central area, wherein the ring body includes a relatively rigid inner core member having a U-shaped radial cross-section open toward the inflow side and an in-plane bending stiffness measured by moving one free end in the radial plane with respect to the other free end that is at least 10 times the torsional out-of-plane bending stiffness measured by moving one free end perpendicular to the radial plane with respect to the other free end.

10. The tricuspid annuloplasty ring of claim 9, wherein the core member has an in-plane bending stiffness that is between about 10-200 times the torsional out-of-plane bending stiffness.

11. The tricuspid annuloplasty ring of claim 9, wherein the core member has an in-plane bending stiffness that is between about 20-60 times the torsional out-of-plane bending stiffness.

12. The tricuspid annuloplasty ring of claim 9, wherein the second segment is generally planar with the first segment rising up therefrom in a complex curve and the third segment descending down therefrom in a complex curve, and wherein the complex curves in both the first and third segments terminate in upturned free ends.

13. The tricuspid annuloplasty ring of claim 9, further including a suture-permeable interface surrounding the core member, and an outer fabric covering, wherein the suture-permeable interface includes an outwardly projecting flange on an inflow edge of the ring body, and the ring further includes a visible marker line on the fabric cover at the base of the flange on its outflow side.

14. The tricuspid annuloplasty ring of claim 9, wherein the U-shaped radial cross-section of the core member in the second segment has a first height $h_1$ and in the first and third segments has lesser heights relative to $h_1$ and includes gradual transitions between the U-shaped radial cross-section of the first height $h_1$ and the U-shaped cross-sections of lesser heights.

15. The tricuspid annuloplasty ring of claim 9, wherein at any one point around the core member the U-shaped radial cross-sections include side walls having a thickness $t_1$ and a web having a thickness $t_2$, and wherein the thicknesses $t_1$ and $t_2$ vary gradually around the core member.

* * * * *